US008999320B2

(12) United States Patent
Sakmar et al.

(10) Patent No.: US 8,999,320 B2
(45) Date of Patent: Apr. 7, 2015

(54) NANOSCALE BOUND BILAYERS, METHODS OF USE AND PRODUCTION

(75) Inventors: Thomas P. Sakmar, New York, NY (US); Thomas Huber, New York, NY (US); Sourabh Banerjee, New York, NY (US)

(73) Assignee: The Rockefeller University, New York, NY (US)

( * ) Notice: Subject to any disclaimer, the term of this patent is extended or adjusted under 35 U.S.C. 154(b) by 598 days.

(21) Appl. No.: 12/865,615

(22) PCT Filed: Jan. 30, 2009

(86) PCT No.: PCT/US2009/032745
§ 371 (c)(1),
(2), (4) Date: Nov. 22, 2010

(87) PCT Pub. No.: WO2009/097587
PCT Pub. Date: Aug. 6, 2009

(65) Prior Publication Data
US 2011/0059159 A1    Mar. 10, 2011

Related U.S. Application Data

(60) Provisional application No. 61/062,922, filed on Jan. 30, 2008.

(51) Int. Cl.
*A61K 9/127* (2006.01)
*A61K 38/00* (2006.01)
*A61K 47/00* (2006.01)

(52) U.S. Cl.
CPC .................................... *A61K 9/127* (2013.01)

(58) Field of Classification Search
USPC .......... 424/94.1, 94.3, 450; 435/183; 530/359
See application file for complete search history.

(56) References Cited

U.S. PATENT DOCUMENTS

| 7,048,949 | B2 | 5/2006 | Sligar et al. | |
| 7,083,958 | B2 | 8/2006 | Sligar et al. | |
| 2004/0053384 | A1 | 3/2004 | Sligar et al. | |
| 2005/0142639 | A1* | 6/2005 | Graversen et al. | 435/69.1 |
| 2005/0182243 | A1 | 8/2005 | Sligar et al. | |
| 2007/0117179 | A1 | 5/2007 | Kudlicki et al. | |
| 2008/0248565 | A1* | 10/2008 | Katzen et al. | 435/325 |

FOREIGN PATENT DOCUMENTS

WO    2009/097587 A2    8/2009

OTHER PUBLICATIONS

Navratilova et al, Analyt. Biochem. 339:271-281, 2005.*
Oda et al., "Reconstituted High Density Lipoprotein Enriched with the Polyene Antibiotic Amphotericin B", Journal of Lipid Research, Feb. 2006, pp. 260-267, vol. 47, No. 2.
UniPROTKB [online], "Apolipoprotein A-I Precursor—Danio rerio (Zebrafish)", Jan. 1998, Last Modified May 5, 2009, Version 61 Available on the Internet at <<URL:http://www.uniprot.org/uniprot/O42363>>.
Bayburt et al.,"Single-Molecule Height Measurements on Microsomal Cytochrome P450 in Nanometer-Scale Phospholipid Bilayer Disks", Proceedings of the National Academy of Sciences, 2002, pp. 6725-6730, vol. 99, No. 10.
Jonas et al., "Kinetics and Mechanism of Apolipoprotein A-I Interaction with L-a-Dimyristoylphosphatidylcholine Vesicles", Journal of Biological Chemistry, 1980, pp. 2190-2194, vol. 255, No. 5.
Khurana et al., "Identification of a Linear Peptide Recognized by Monoclonal Antibody 2D7 Capable of Generating CCR5-Specific Antibodies with Human Immunodeficiency Virus-Neutralizing Activity", Journal of Virology, 2005, pp. 679*1-9800, vol. 79, No. 11.
Navratilova et al., "Solubilization, Stabilization, and Purification of Chemokine Receptors Using Biosensor Technology," Analytical Biochemistry, 2005, pp. 271-281, vol. 339.
Navratilova et al., "Analyzing Ligand and Small Molecule Binding Activity of Solubilized GPCRs Using Biosensor Technology", Analytical Biochemistry, 2006, pp. 132-139, vol. 355.
Knepp et al., "Direct Measurement of Thermal Stability of Expressed CCR5 and Stabilization by Small Molecule Ligands", Biochemistry, 2011, pp. 502-511, vol. 50, No. 4.
Knepp et al., Supporting Information for "Direct Measurement of Thermal Stability of Expressed CCR5 and Stabilization by Small Molecule Ligands", Biochemistry, 2011, pp. 502-511, vol. 50, No. 4.
Segrest et al., "A Detailed Molecular Belt Model for Apolipoprotein A-I in Discoidal High Density Lipoprotein", The Journal of Biological Chemistry, 1999, 31755-31758, vol. 274, No. 45.
Banerjee, Sourabh, "Studies of G Protein-Coupled Receptors Incorporated into a Novel, Nanoscale, Membrane-Mimetic System: Characterizations of Nanoscale Apolipoprotein Bound Bilayers and the Effect of the Membrane Environment on GPCR Function", Thesis Presented to the Faculty of The Rockefeller University, Sep. 2008, 234 pages.
Banerjee et al., "Non-vesicular transfer of membrane proteins from nanoparticles to lipid bilayers", The Journal of General Physiology, Jan. 31, 2011, pp. 217-223, vol. 137 No. 2.
Banerjee et al., "Rapid Incorporation of Functional Rhodopsin into Nanoscale Apolipoprotein Bound Bilayer (NABB) Particles", Journal of Molecular Biology, 2008, pp. 1067-1081, vol. 377.
Bricarello et al., "Reconstituted Lipoprotein: A Versatile Class of Biologically-Inspired Nanostructures", ACS Nano, 2011, pp. 42-57, vol. 5 No. 1.
Knepp et al., "Direct Measurement of Thermal Stability of Expressed CCR5 and Stabilization by Small Molecule Ligands", Biochemistry, 2011, pp. 502-511, vol. 50.

(Continued)

*Primary Examiner* — Kevin Hill
(74) *Attorney, Agent, or Firm* — Thompson Coburn LLP; Charles P. Romano

(57) ABSTRACT

Methods for rapidly obtaining a nanoscale apolipoprotein bound phospholipid bilayer (NABB) associated with at least one membrane protein are provided. Also disclosed are methods for rapidly obtaining a NABB not associated with membrane proteins. Immunogenic compositions comprising NABBs with native conformational epitopes are also provided along with their methods of use.

14 Claims, 8 Drawing Sheets

(56) References Cited

OTHER PUBLICATIONS

Popot, Jean-Luc, "Amphipols, Nanodiscs, and Fluorinated Surfactants: Three Nonconventional Approaches to Studying Membrane Proteins in Aqueous Solutions", Annual Review of Biochemistry, 2010, pp. 737-775, vol. 79.

Zaitseva et al., "SEIRA Spectroscopy on a Membrane Receptor Monolayer Using Lipoprotein Particles as Carriers", Biophysical Journal, Oct. 2010, pp. 2327-2335, vol. 99.

\* cited by examiner

Figure 1    Amino Acid Sequence Alignment of Zebrafish apo A-1 and Human apo A-1
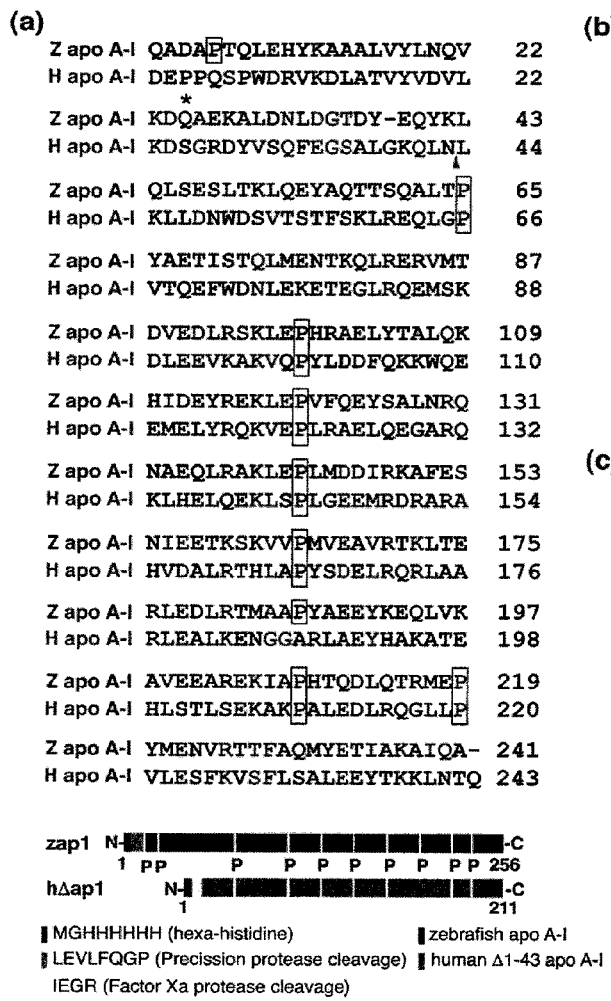
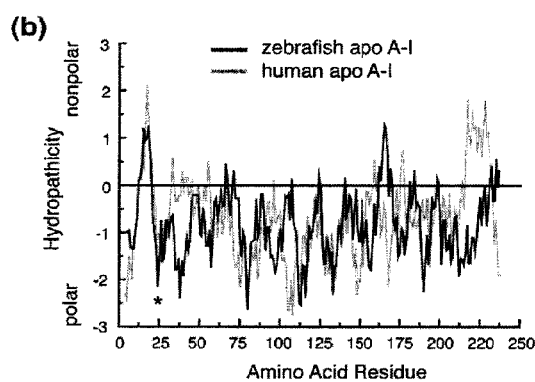
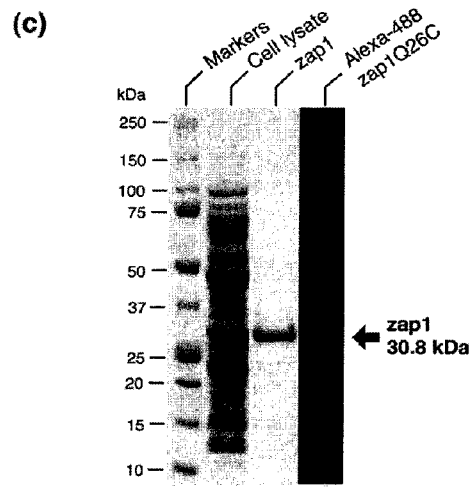

Figure 2    Formation of Lipoprotein Particles by Zebrafish apo A-1 with POPC.
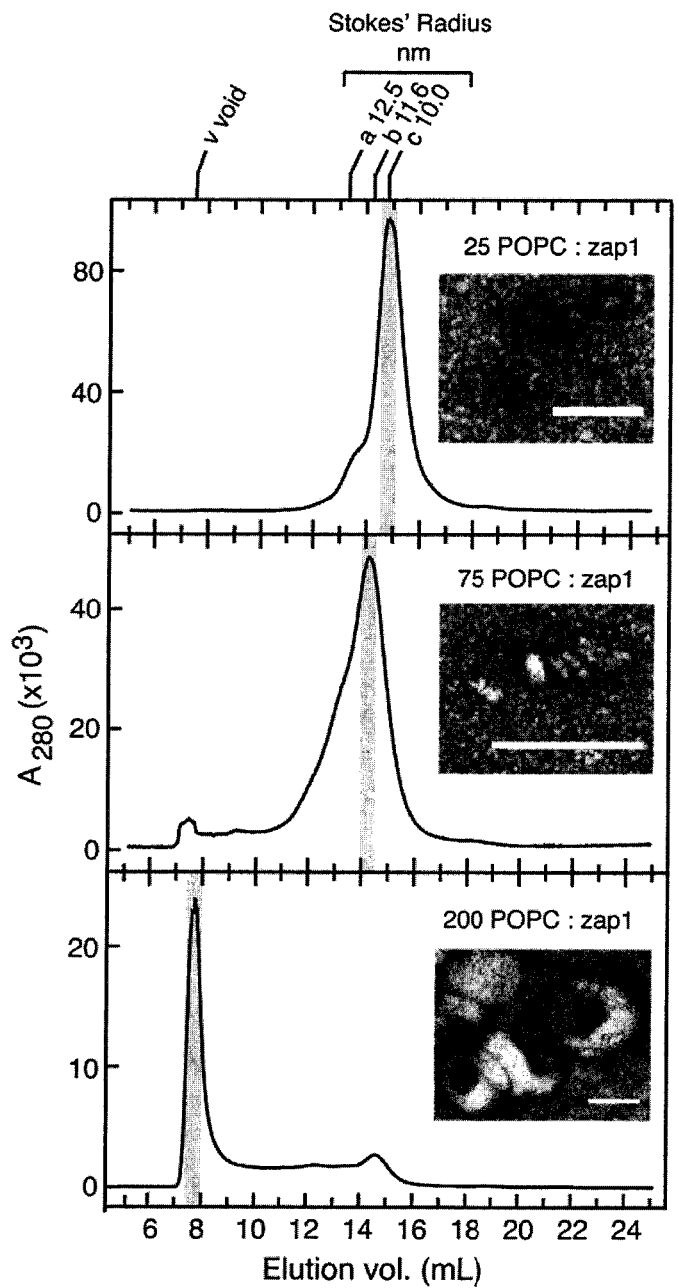

Figure 3   Characterization of Rho incorporation into NABBS
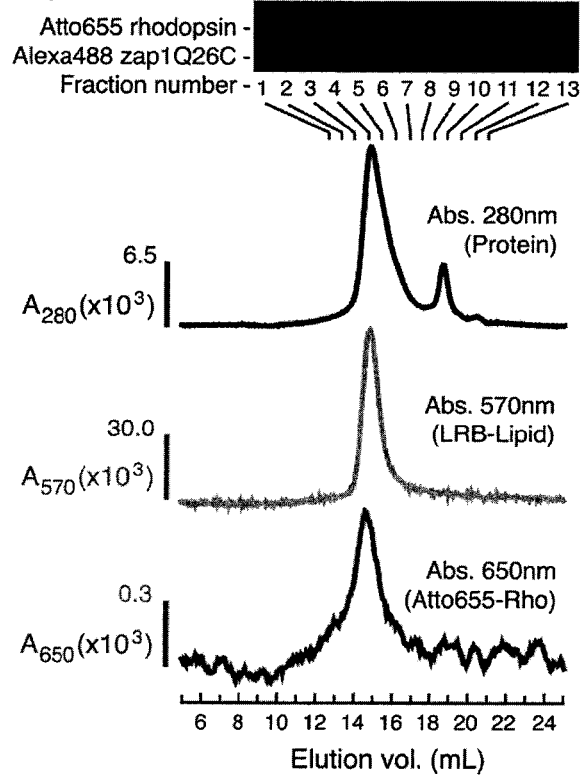
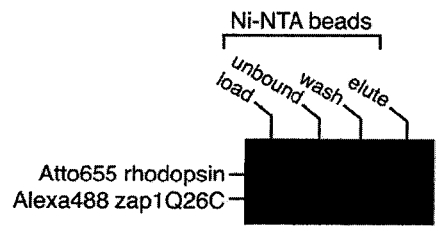
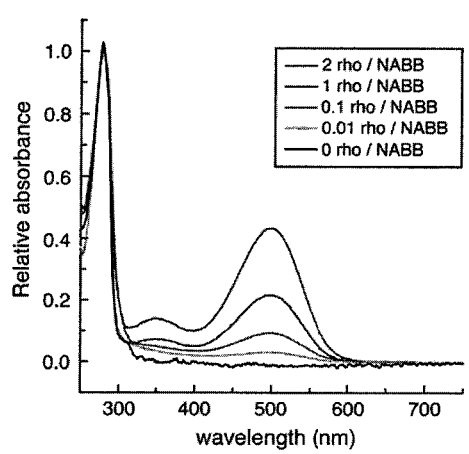

Figure 4 Visualization and Stoichiometry of Rho-incorporated NABBs
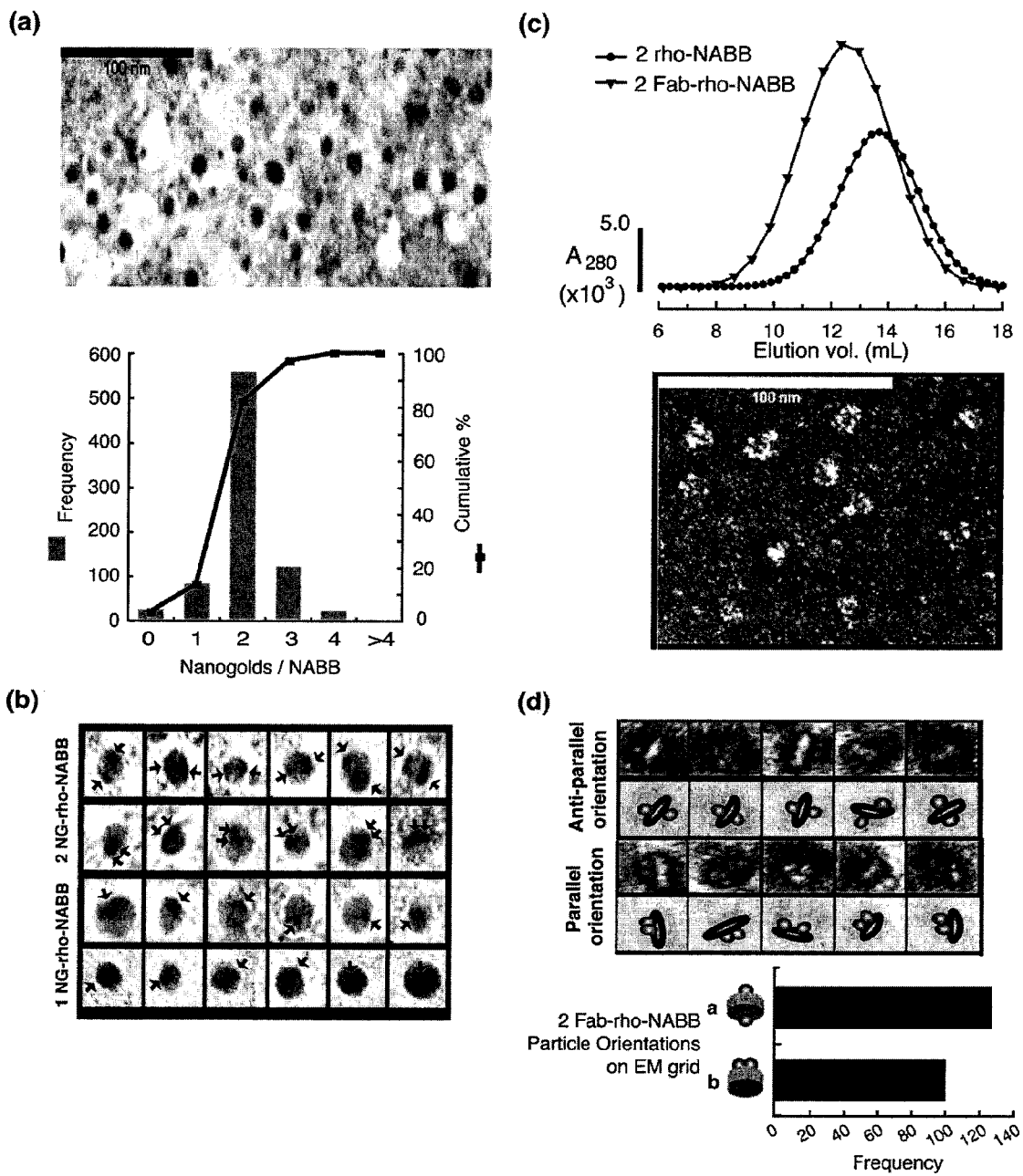

Figure 5    Biochemical Characterization of Rho-NABB
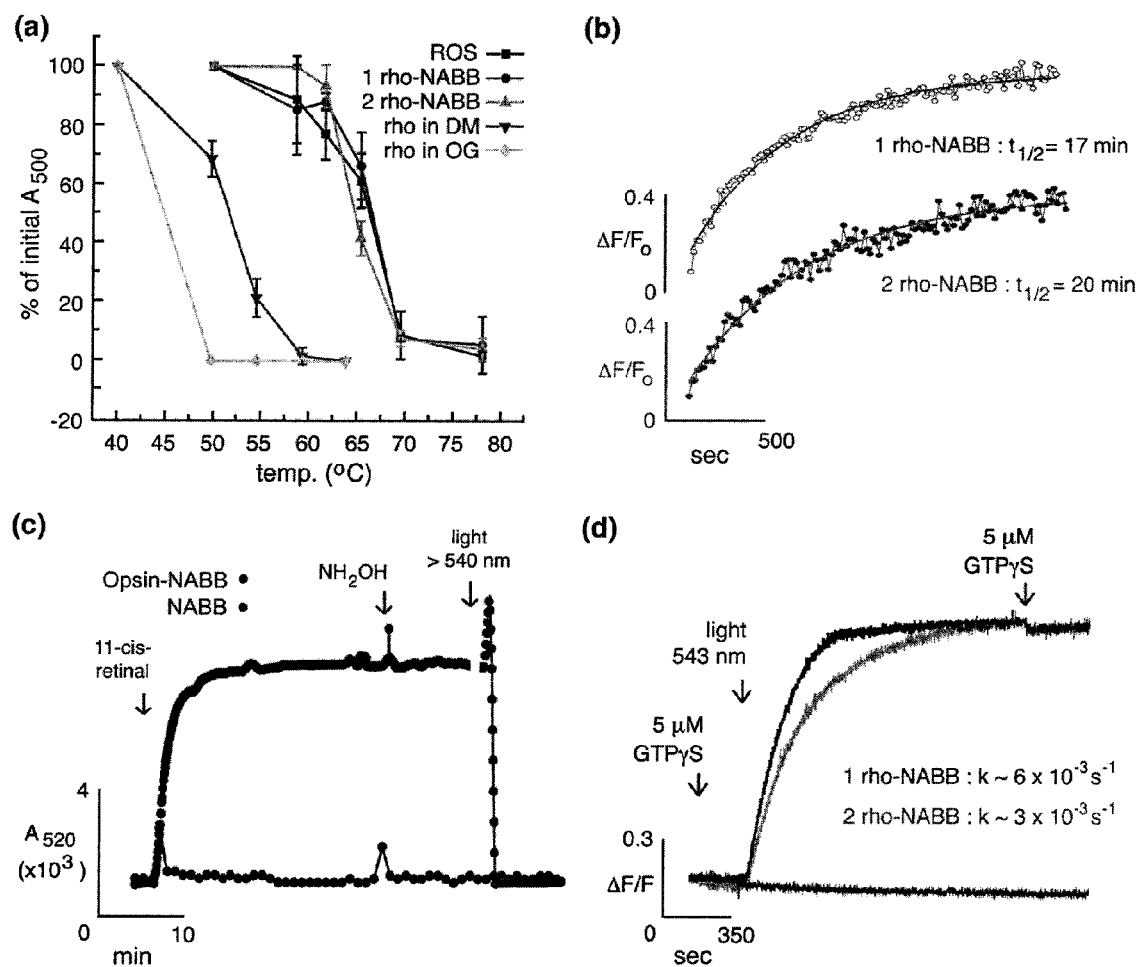

Figure 6    Gel-filtration of CCR5-NABBs
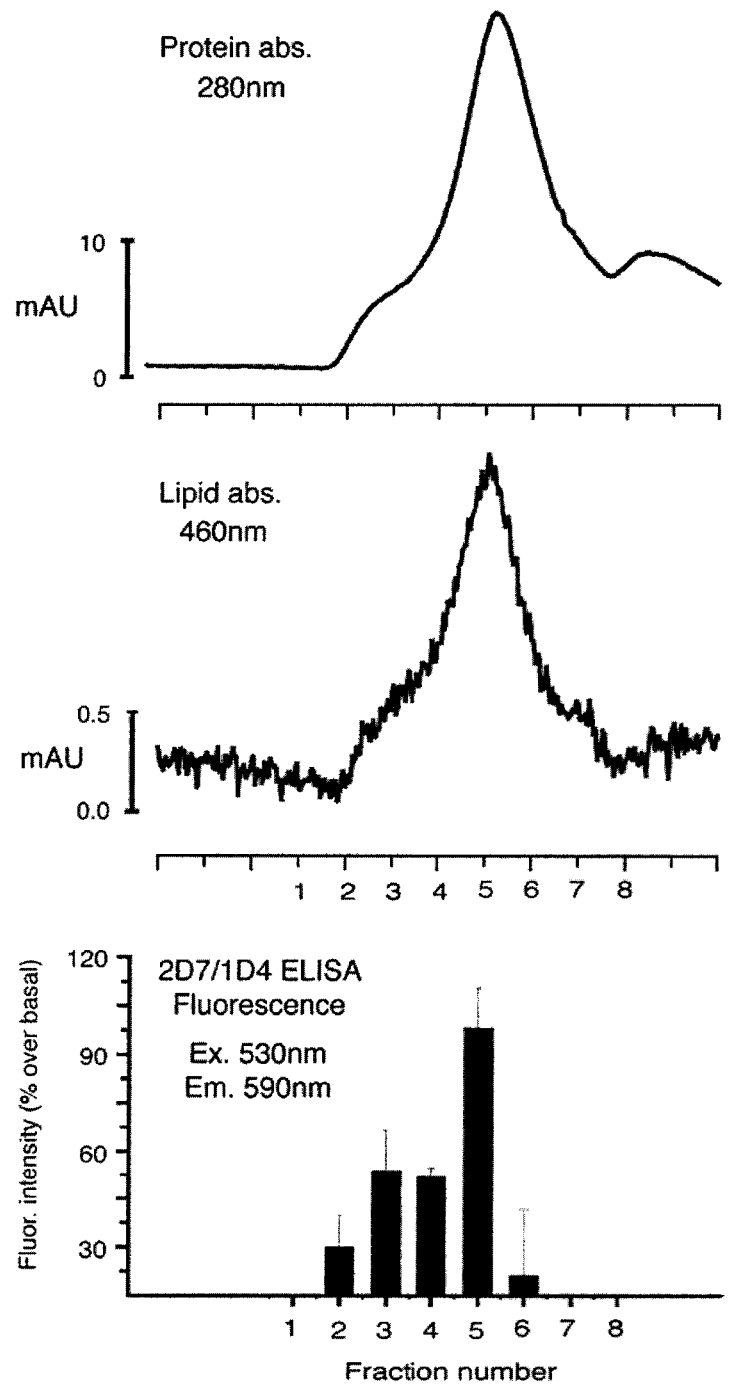

Figure 7    Schematic of Sandwich-ELISA Assay for Characterizing CCR5-NABB
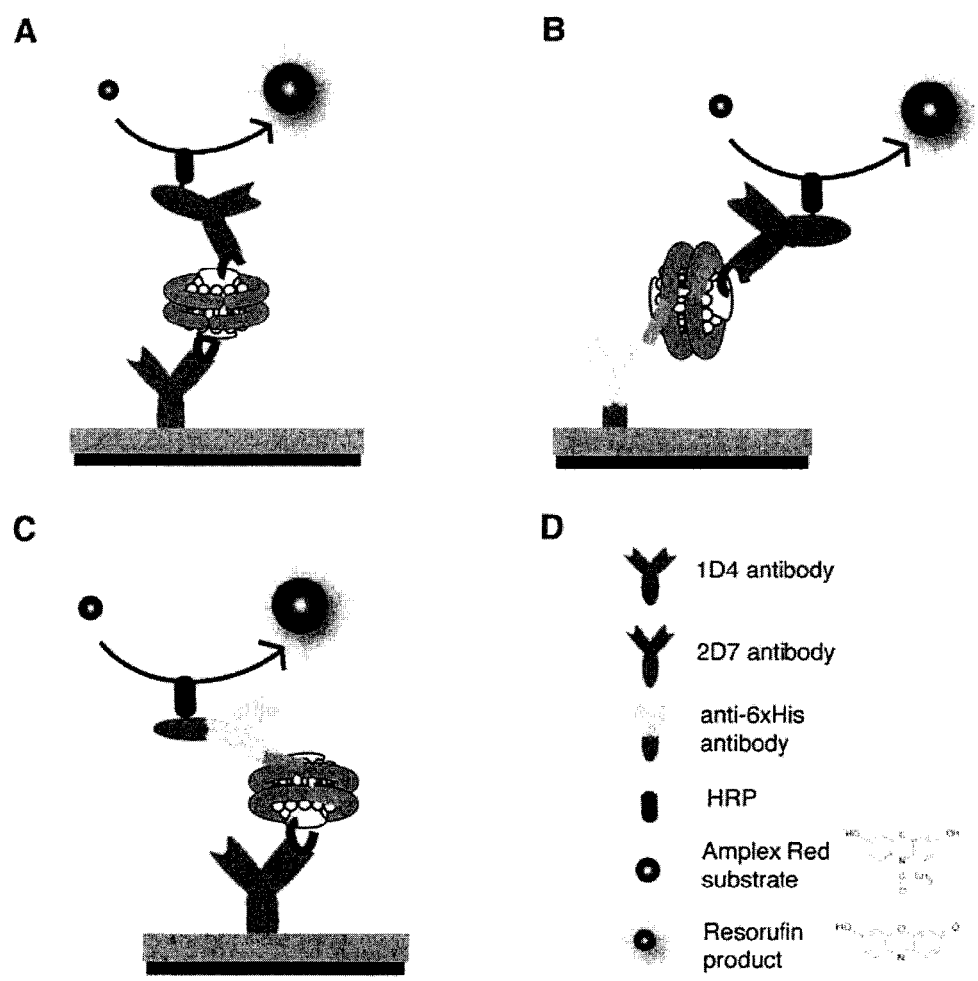

Figure 8    Ligand Mediated Activation of CCR5-NABBs
A
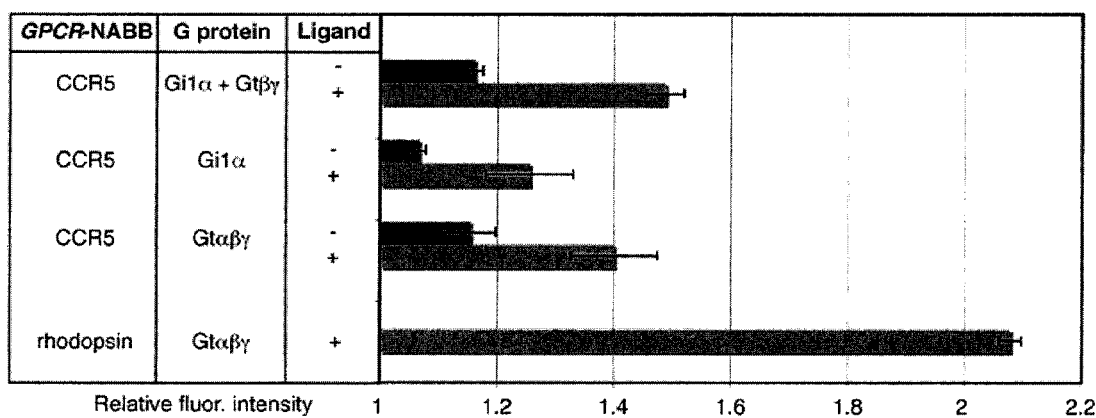
B
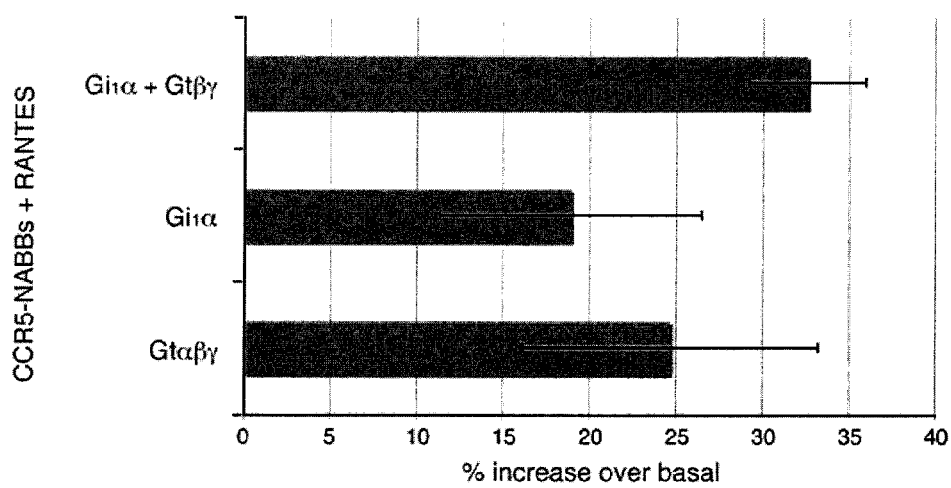

NANOSCALE BOUND BILAYERS, METHODS OF USE AND PRODUCTION

CROSS-REFERENCE TO RELATED APPLICATIONS

This application is a National Stage application of International Patent Application No PCT/US2009/032745, filed Jan. 30, 2009, incorporated herein by reference in its entirety, which claims the benefit of U.S. Provisional Application Ser. No. 61/062,922 filed Jan. 30, 2008, which is herein incorporated by reference in its entirety.

INCORPORATION OF SEQUENCE LISTING

A computer readable form of the sequence listing named "49248_91213_SEQ_LST_V2.txt" and which is 44,447 bytes in size (measured in MS-DOS) and created on Nov. 20, 2012, is electronically filed herewith and herein incorporated by reference. This Sequence Listing consists of SEQ ID NOs: 1-27.

BACKGROUND OF THE INVENTION

Lipids as a class of molecules display a wide diversity in both structure and biological function. The propensity of hydrophobic lipid tails to self-associate and the tendency of the hydrophilic moieties to interact with aqueous environments and with each other, is the physical basis of the spontaneous formation of the lipid bilayer membrane. The membrane is the supporting matrix for a wide spectrum of proteins involved in many cellular processes. Lipids also allow particular proteins in membranes to aggregate, and others to disperse. Approximately 20-35% of all proteins are integral membrane proteins, and probably half of the remaining proteins function at or near a membrane surface. Lipids can also act as first and second messengers in signal transduction and molecular recognition processes.

Discoidal lipid particles are hypothesized to be intermediates in a micelle-to-vesicle transition reaction of lipids upon detergent removal, as deduced from static and dynamic light scattering experiments (Leng et al. *Biophys. J.* 85, 1624-1646 (2003)). When a detergent is removed from a mixed-micellar state of lipids and detergents, disc-like intermediate micelles rapidly form. These disc-like micelles grow by coalescence. Large discs then become unstable due to incomplete coverage of their perimeter by detergent which increases the energy per unit length of boundary (line tension) of the disc, leading to closure of the large lipid disc to form a lipid vesicle.

Apolipoproteins are uniquely flexible proteins characterized by a series of proline-punctuated amphipathic, α-helical domains capable of associating with lipid acyl chains. Apolipoproteins have been classified as "protein detergents" capable of isolating membrane proteins in a soluble and planar lipid environment. The formation of discoidal structures of lipids surrounded by human apolipoprotein A-I (apo A-I) was first demonstrated in 1980 (Jonas and Drengler *J. Biol. Chem.* 255, 2190-2194 (1980)), after similar structures were implicated in transport of cholesterol by High Density Lipoproteins (HDL) in the serum (Jonas et al. *Federation Proceedings* 36, 829-829 (1977)). An engineered N-terminal truncated form of human apo A-I was used in a similar manner to incorporate peripheral and integral membrane proteins into such bilayer nano discs (Bayburt et al. *Nano Lett.* 2, 853-856 (2002); Bayburt and Sligar *Proc. Natl. Acad. Sci. USA* 99, 6725-6730 (2002); Bayburt and Sligar *Protein Sci.* 12, 2476-2481 (2003)). The presence of apo A-I at a certain concentration possibly replaces the surfactant stabilizing the edge of the bilayer due to lipid-binding properties of its amino acids to provide kinetic stability to the disc-like micelle formed.

Incorporation of peripheral and integral membrane proteins into nanoscale discoidal lipoproteins or nanoscale apolipoprotein bound phospholipid bilayers (NABB) have several advantages over incorporation of those proteins into lipid vesicles. The discrete nanoscale lipid discs prevent aggregation phenomena as seen with detergent micelles and light-scattering of lipid vesicles, thus providing a system that can be isolated in a monodisperse form suitable for multi-well assays.

Another problem is that vesicles form closed structures and the chemical composition of the lumen is difficult to alter. Lipid vesicles are also prone to light scattering artifacts in optical spectroscopy and a precise control of the number of receptors per vesicle, and heterogeneity of vesicle sizes, are difficulties. A further complication, when membrane proteins such as a GPCR are reconstituted in a vesicle, arises from the 'sidedness' of the membrane protein interactions with ligands and G proteins respectively.

Chemokine receptors are members of family A GPCRs and of significant clinical importance. Chemokines (chemotactic cytokines) constitute a superfamily of structurally related small proteins, less than 100 residues in length that are implicated in the control of a large variety of biological processes including inflammation, immunosurveillance, viral infection and cancer (Gerard and Rollins *Nat. Immunology* 2, 108-115 (2001)). CCR5 is an important co-receptor that is exploited for entry of HIV-1 (Human Immunodeficiency Virus type 1) and is critical for the transmission of this virus in the body (Berger et al. *Ann. Rev. Immunol.* 17, 657-700 (1999)). No adverse health effects have been linked to the non-functional CCR5 in these individuals, which makes CCR5 a very attractive target for pharmaceutical intervention for the prevention of HIV/AIDS (O'Brien and Moore *Immunol. Reviews* 177, 99-111 (2000)).

A CCR5 to CXCR4 switch has also been reported to accompany the onset of AIDS (Berger et al. *Ann. Rev. Immunol.* 17, 657-700 (1999)). SDF-1 (Stromal cell-Derived Factor-1) is a CXC-chemokine and is expressed as two functionally identical, alternative splice variants: SDF-1α and SDF-1β (Rossi and Zlotnik *Ann. Rev. Immunol.* 18, 217-243 (2000)), and binds to CXCR4. CXCR4 is expressed in hematopoietic cell-lines (Zou et al. *Nature* 393, 595-599 (1998)) and is thought to be involved in signaling responsible in part for stem-cell maturation, naive T-cell migration to spleen for antigen presentation and other developmental signaling (Proudfoot *Nat. Rev. Immunology* 2, 106-115 (2002)). The SDF-1/CXCR4 system has been implicated in breast and ovarian cancers (Muller *Biochem. Pharmacol.* 72, 739-748 (2001); Scotton et al. *Cancer Res.* 62, 5930-5938 (2002)) and brain tumors (Rubin et al. *Proc. Natl. Acad. Sci. USA* 100, 13513-13518 (2003)).

Chemokine receptors thus provide targets for generating effective antibody responses. Ideally, intact receptors or variants must be presented in a correctly folded, homogeneous, and soluble form at a high concentration capable of eliciting an immune response. Moreover, vaccine candidates must conform to certain levels of purity and defined composition.

Various methods of generating nanoscale apolipoprotein bound phospholipid bilayer (NABB) with associated membrane proteins have been described. Kudlicki et al., disclose in vitro protein synthesis systems where the membrane protein is synthesized in the presence of the NABB (US Patent Application Publication 2007/0117179). However, it is not evident that the in vitro synthesis system can provide for homogeneous populations of NABB with defined lipid and associated protein content or that the associated protein will retain it's native conformation and/or activity. Sligar et al., disclose an in vitro assembly method where the NABBs associated with membrane proteins are obtained after a lengthy dialysis step that provides for removal of solubilizing detergents and subsequent self-assembly of the NABB with associated membrane proteins (U.S. Pat. Nos. 7,083,958 and 7,048,949; US Patent Application Publication US 2005/0182243). However, the lengthy dialysis step used in this in vitro assembly method is inconvenient and may disrupt the native conformation and/or activity of the associated membrane protein.

Accordingly, a need exists for new methods of forming nanoscale apolipoprotein bound phospholipid bilayers (NABBs) that provide for homogenous populations of NABBs with defined lipid and protein compositions. New methods for associating membrane proteins into NABB that provide for increased activity and/or native conformations of the integrated proteins are also needed, as are the resultant NABB compositions comprising integrated membrane proteins with increased activity and/or native protein conformations.

SUMMARY OF THE INVENTION

The invention generally provides methods for obtaining a nanoscale apolipoprotein bound phospholipid bilayer (NABB), isolated nanoscale apolipoprotein bound phospholipid bilayers associated with at least one agent, and a substantially homogenous population of nanoscale apolipoprotein bound phospholipid bilayers. Also provided are resultant compositions comprising homogenous populations of NABB and NABB with associated agents.

In certain embodiments, the invention provides methods for obtaining a nanoscale apolipoprotein bound phospholipid bilayer (NABB) comprising: a) obtaining a mixture comprising a apolipoprotein A-1, one or more agents, and one or more detergents, wherein the mixture is substantially deficient in NABB molecules; b) depleting the detergent from the mixture to obtain a detergent depleted mixture comprising a nanoscale apolipoprotein bound phospholipid bilayer associated with at least one agent, wherein the detergent is depleted from the mixture within about one hour of obtaining the mixture in step (a); and, c) purifying a nanoscale apolipoprotein bound phospholipid bilayer associated with at least one agent from the detergent depleted mixture. In certain embodiments, the agent can be a membrane protein. At least one agent can be an integral membrane protein or a peripheral membrane protein, in certain embodiments. In certain embodiments, a peripheral membrane protein can be associated with the NABB by a lipid anchor. An integral membrane protein used can be selected from the group consisting of a Type I integral membrane protein, a Type II integral membrane protein, a seven transmembrane domain (7-TM) integral membrane protein, a G-protein coupled receptor, an ion-channel, and an ion-pump. In certain embodiments, at least one of the agents is a hydrophobic compound. When one agent is a hydrophobic compound, the compound can be a diagnostic reagent, an anti-fungal compound, an anti-cancer compound, an immunosuppressive compound, an antiviral compound, an anesthetic compound, a sedative, a lipophilic vitamin, a glucocorticoid, a mineral corticoid or a hormone. In certain embodiments, the hydrophobic compound is amphotericin, miconazole, paclitaxel, taxol, doxorubicin, cyclosporine, nelfinavir, propofol, diazepam, retinal, retinol, retinoic acid, phytonadione, or a derivative thereof. In certain embodiments, the phospholipid comprises at least one of phosphatidyl choline, phosphatidyl ethanolamine, phosphatidyl inositol, 1,2-dipalmitoyl-phosphatidylcholine (DPPC), 1-palmitoyl-2-oleoyl-phosphatidyl choline (POPC), 1-palmitoyl-2-oleoyl-phosphatidyl serine (POPS), 1-palmitoyl-2-oleoyl-phosphatidyl ethanolamine (POPE), dihexanoyl phosphatidyl choline (DHPC), 1,2-dipalmitoyl-phosphatidyl ethanolamine (DPPE), dipalmitoyl phosphatidyl inositol, 1,2-dimyristoyl phosphatidyl ethanolamine (DMPE), dimyristoyl phosphatidyl inositol, dihexanoyl phosphatidyl ethanolamine (DHPE), dihexanoyl phosphatidyl inositol, 1-palmitoyl-2-oleoyl-phosphatidyl inositol, 1,2-dimyristoyl-3-phosphatidyl choline (DMPC), 1,2-dioleoyl phosphatidyl ethanolamine (DOPE), a labelled derivative thereof, or a combination thereof. In certain embodiments, the detergent comprises at least one of FOS-CHOLINE, FOS-MEA, CYFOS, FENFOS, FOSFEN, a sugar-based detergent; a polyoxyethylene based detergent, a bile-salt based detergent, or a combination thereof. A sugar based detergent can include n-octyl-beta-D-glucopyranoside (OG), n-nonyl-beta-D-glucopyranoside, n-dodecyl-beta-D-maltopyranoside (DDM), or 5-Cyclohexylpentyl beta-D-maltopyranoside (Cymal-5). A bile-salt based detergent can be sodium cholate, 3-[(3-Cholamidopropyl)dimethylammonio]-1-propane sulfonate (CHAPS), 3-[(3-Cholamidopropyl)dimethylammonio]-2-hydroxy-1-propane sulfonate (CHAPSO), or a derivative thereof. A polyoxyethylene based detergent can be Tween 20, Triton X-100, or a derivative thereof. In certain embodiments, the apolipoprotein A-I can be a human, a bovine, an equine, a canine, a feline, a porcine or fish apolipoprotein A-I. When the apolipoprotein A-1 is a fish apolipoprotein A-1, the apolipoprotein can comprise SEQ ID NO:1, 3, 6-23, or 24. In certain embodiments, a Zebrafish apolipoprotein A-I protein is used. A Zebrafish apolipoprotein that comprises an amino acid sequence wherein the residue corresponding to glutamine 25 of SEQ ID NO:1 has been substituted with a cysteine residue can be used in certain embodiments. In certain embodiments, the obtaining and/or the depleting step are performed at a temperature of about 2° C. to about 30° C. In certain embodiments, the detergent is depleted from the mixture within about 30 minutes of obtaining the mixture in step (a). In certain embodiments, an activity of a membrane protein associated with an NABB purified in step (c) is increased relative to the activity of the membrane protein associated with an NABB that is obtained by dialysis-mediated detergent depletion. In certain embodiments, an activity of a membrane protein associated with an NABB purified in step (c) is increased relative to the activity of the membrane protein in detergent. In certain embodiments, apolipoprotein A-I are at a molar ratio of about 25:1 phospholipid:apolipoprotein A-I to about 200:1 phospholipid:apolipoprotein A-I in the mixture of step (a). In still other embodiments, the phospholipid and the apolipoprotein A-I are at a molar ratio of about 50:1 phospholipid:apolipoprotein A-I to about 160:1 phospholipid:apolipoprotein A-I in the mixture of step (a). In certain embodiments a phospholipid:apolipoprotein A-I:membrane protein ratio can be used in (a) that provides for a substantially homogeneous population of purified NABB in (c) wherein at least 70% of the NABB are associated with one membrane protein. In certain embodiments a phospholipid:apolipoprotein A-I:membrane protein ratio can be used in (a) that provides for a substantially homogeneous population of purified NABB in (c) wherein at least 70% of the NABB are associated with two membrane proteins.

Also provided are isolated nanoscale apolipoprotein bound phospholipid bilayers (NABB) associated with at least one agent, wherein the NABB associated with at least one agent is obtained by any of the methods provided herein. In certain embodiments, an activity of a membrane protein associated with the isolated NABB is increased relative to the activity of the membrane protein associated with an NABB that is obtained by dialysis-mediated detergent depletion. In certain embodiments, an activity of a membrane protein associated with the isolated NABB is increased relative to the activity of the membrane protein in detergent. In certain embodiments, a membrane protein associated with the NABB contains a native conformational epitope not preserved in a detergent solubilized state of the membrane protein. In certain embodiments, a membrane protein associated with the NABB contains a native conformational epitope not preserved in the membrane protein when the membrane protein associated with an NABB is obtained by dialysis-mediated detergent depletion.

Also provided herein are methods of using nanoscale apolipoprotein bound phospholipid bilayer (NABB) associated with at least one agent made by any of the methods provided herein for delivery of a therapeutic or diagnostic agent to a subject in need thereof. In certain embodiments, the methods comprise use of a composition comprising a nanoscale apolipoprotein bound phospholipid bilayer (NABB) associated with at least one agent for delivery of a therapeutic or diagnostic agent to a subject in need thereof, wherein the NABB associated with at least one agent is made by any of the methods provided herein.

Also provided herein are methods for obtaining a nanoscale apolipoprotein bound phospholipid bilayer (NABB) that comprise a) obtaining a mixture comprising an apolipoprotein A-I, one or more phospholipid(s), and one or more detergents, wherein the mixture is substantially deficient in NABB molecules; b) depleting the detergent from the mixture to obtain a detergent depleted mixture comprising a nanoscale apolipoprotein bound phospholipid bilayer, wherein the detergent is depleted from the mixture within about one hour of obtaining the mixture in step (a); and, c) purifying a nanoscale apolipoprotein bound phospholipid bilayer from the detergent depleted mixture. In certain embodiments, the phospholipid comprises at least one of phosphatidyl choline, phosphatidyl ethanolamine, phosphatidyl inositol, 1,2-dipalmitoyl-phosphatidylcholine (DPPC), 1-palmitoyl-2-oleoyl-phosphatidyl choline (POPC), 1-palmitoyl-2-oleoyl-phosphatidyl serine (POPS), 1-palmitoyl-2-oleoyl-phosphatidyl ethanolamine (POPE), dihexanoyl phosphatidyl choline (DHPC), 1,2-dipalmitoyl-phosphatidyl ethanolamine (DPPE), dipalmitoyl phosphatidyl inositol, 1,2-dimyristoyl phosphatidyl ethanolamine (DMPE), dimyristoyl phosphatidyl inositol, dihexanoyl phosphatidyl ethanolamine (DHPE), dihexanoyl phosphatidyl inositol, 1-palmitoyl-2-oleoyl-phosphatidyl inositol, 1,2-dimyristoyl-3-phosphatidyl choline (DMPC), 1,2-dioleoyl phosphatidyl ethanolamine (DOPE), a labelled derivative thereof, or a combination thereof. In certain embodiments, the detergent comprises at least one of FOS-CHOLINE, FOS-MEA, CYFOS, FENFOS, FOSFEN, a sugar-based detergent, a polyoxyethylene based detergent, a bile-salt based detergent, or a combination thereof. A sugar based detergent can be n-octyl-beta-D-glucopyranoside (OG), n-nonyl-beta-D-glucopyranoside, n-dodecyl-beta-D-maltopyranoside (DDM), or 5-Cyclohexylpentyl beta-D-maltopyranoside (Cymal-5). A bile-salt based detergent can be sodium cholate, 3-[(3-Cholamidopropyl)dimethylammonio]-1-propane sulfonate (CHAPS), 3-[(3-Cholamidopropyl)dimethylammonio]-2-hydroxy-1-propane sulfonate (CHAPSO), or a derivative thereof. A polyoxyethylene based detergent can be Tween 20, Triton X-100, or a derivative thereof. In certain embodiments, the obtaining and/or the depleting step are performed at a temperature of about 2° C. to about 30° C. In certain embodiments, the detergent is depleted from the mixture within about 30 minutes of obtaining the mixture in step (a). In certain embodiments, the phospholipid and the apolipoprotein A-I are at a molar ratio of about 25 phospholipid:1 apolipoprotein A-I to about 200 phospholipid:1 apolipoprotein A-I in the mixture of step (a). In certain embodiments, phospholipid and the apolipoprotein A-I are at a molar ratio of about 50 phospholipid:1 apolipoprotein A-I to about 160 phospholipid:apolipoprotein A-I in the mixture of step (a). In certain embodiments, the phospholipid and said Zebrafish apolipoprotein A-I are at a molar ratio of about 75 phospholipid:1 apolipoprotein A-I. In certain embodiments, a substantially homogenous population of nanoscale apolipoprotein bound phospholipid bilayers (NABBs) are purified. In certain embodiments, the substantially homogenous population comprises at least 70% NABBs with diameter of about 9 to about 17 nm. In certain embodiments, the apolipoprotein A-I protein comprises an amino acid sequence of SEQ ID NO: 1, 2, 3, 6-23, or 24. In still other embodiments, the methods can further comprise the step of combining the nanoscale apolipoprotein bound phospholipid bilayer with a hydrophobic compound to obtain an NABB associated with the hydrophobic compound. A hydrophobic compound used can be a diagnostic reagent, an anti-fungal compound, an anti-cancer compound, an immunosuppressive compound, an antiviral compound, an anesthetic compound, a sedative, a lipophilic vitamin, a glucocorticoid, a mineral corticoid or a hormone. In certain embodiments, the hydrophobic compound is amphotericin, miconazole, paclitaxel, taxol, doxorubicin, cyclosporine, nelfinavir, propofol, diazepam, 11-cis retinal, retinol, retinoic acid, phytonadione, or a derivative thereof. Also provided herein are methods of using nanoscale apolipoprotein bound phospholipid bilayer (NABB) associated with a hydrophobic compound that are made by any of the methods provided herein for delivery of a therapeutic or diagnostic agent that is a hydrophobic compound to a subject in need thereof. In certain embodiments, the methods comprise use of a composition comprising a nanoscale apolipoprotein bound phospholipid bilayer (NABB) associated with at least one hydrophobic compound for delivery of a therapeutic or diagnostic agent to a subject in need thereof, wherein the NABB associated with at least one agent is made by any of the methods provided herein, and wherein the therapeutic or diagnostic agent is a hydrophobic compound. Also provided herein are substantially homogenous populations of NABBs and/or substantially homogenous populations of NABBs associated with a hydrophobic compound.

Also provided are methods for obtaining a nanoscale apolipoprotein bound phospholipid bilayer (NABB) associated with at least one agent, the method comprising: a) obtaining a cell membrane protein fraction comprising one or more agents; b) combining an apolipoprotein A-I, with the cell membrane protein fraction to obtain a mixture, wherein the mixture is substantially deficient in NABB and comprises one or more phospholipid(s) and one or more detergent(s); c) depleting the detergent(s) from the mixture to obtain a detergent depleted mixture comprising a NABB associated with at least one agent, wherein the detergent(s) is depleted from the mixture within about one hour of obtaining the mixture in step (b); and d) purifying the NABB associated with at least one agent from the detergent depleted mixture. In certain embodiments, the agent can be a membrane protein. At least one agent can be an integral membrane protein or a peripheral membrane protein, in certain embodiments. In certain embodiments, a peripheral membrane protein can be associated with the NABB by a lipid anchor. An integral membrane protein used can be selected from the group consisting of a Type I integral membrane protein, a Type II integral membrane protein, a seven transmembrane domain (7-TM) integral membrane protein, a G-protein coupled receptor, an ion-channel, and an ion-pump. In certain embodiments, at least one of the agents is a hydrophobic compound. When one agent is a hydrophobic compound, the compound can be a diagnostic reagent, an anti-fungal compound, an anti-cancer compound, an immunosuppressive compound, an antiviral compound, an anesthetic compound, a sedative, a lipophilic vitamin, a glucocorticoid, a mineral corticoid or a hormone. In certain embodiments, the hydrophobic compound is amphotericin, miconazole, paclitaxel, taxol, doxorubicin, cyclosporine, nelfinavir, propofol, diazepam, 11-cis retinal, phytonadione, or a derivative thereof. In certain embodiments, the detergent comprises at least one of FOS-CHOLINE, FOS-MEA, CYFOS, FENFOS, FOSFEN, a sugar-based detergent, a polyoxyethylene based detergent, a bile-salt based detergent, or a combination thereof. A sugar based detergent can include n-octyl-beta-D-glucopyranoside (OG), n-nonyl-beta-D-glucopyranoside, n-dodecyl-beta-D-maltopyranoside (DDM), or 5-Cyclohexylpentyl beta-D-maltopyranoside (Cymal-5). A bile-salt based detergent can be sodium cholate, 3-[(3-Cholamidopropyl)dimethylammonio]-1-propane sulfonate (CHAPS), 3-[(3-Cholamidopropyl)dimethylammonio]-2-hydroxy-1-propane sulfonate (CHAPSO), or a derivative thereof. A polyoxyethylene based detergent can be Tween 20, Triton X-100, or a derivative thereof. In certain embodiments, the combining step of (b) comprises an exchange of any detergent and/or lipid and/or phospholipid present in the cell membrane protein fraction with another detergent and/or phospholipid. In certain embodiments, the methods comprise an immunopurification or affinity-based purification step. In certain embodiments, a cell membrane fraction is obtained from a cell comprising at least one recombinant membrane protein. In certain embodiments, the apolipoprotein A-I is a human, a bovine, an equine, a canine, a feline, a porcine, or fish apolipoprotein A-I. In certain embodiments, an apolipoprotein A-I comprising SEQ ID NO: 1, 3, 6-23, or 24 is used.

Also provided are methods of eliciting an immune response in a host comprising administering to the host a composition comprising a purified NABB associated with at least one membrane protein containing a native conformational epitope, wherein the membrane protein does not contain the native conformational epitope when present in a detergent solubilized state. Also provided are methods of eliciting an immune response in a host comprising administering to the host a composition comprising a purified NABB associated with at least one membrane protein containing a native conformational epitope, wherein the membrane protein does not contain the native conformational epitope when the membrane protein is associated with a NABB by dialysis-mediated detergent depletion. In certain embodiments, the membrane protein is an integral or peripheral membrane protein. An integral membrane protein can be selected from the group consisting of a Type I integral membrane protein, a Type II integral membrane protein, a seven transmembrane domain (7-TM) integral membrane protein, a G-protein coupled receptor, an ion-channel, and an ion-pump. In other embodiments, the membrane protein can be a chemokine receptor, a cytokine receptor, a receptor kinase, a receptor phosphatase, a receptor involved in cell-cell interactions, and a cellular adhesion molecule. In certain embodiments, the chemokine receptor interacts with chemokine subfamilies XC (XCR1), CXC (CXCR 1-7), CX3C (CX3CR 1), CC (CCR 1-9, GPR 2). In certain embodiments, the host is a vertebrate. In certain embodiments, the vertebrate is a human, a monkey, a mouse, a rabbit, a goat, a dog, a cat, a bull, a pig, and a chicken.

Also provided are immunogenic compositions can comprising a purified NABB associated with at least one membrane protein containing a native conformational epitope, wherein the membrane protein does not contain the native conformational epitope when the membrane protein is associated with a NABB by dialysis-mediated detergent depletion. In certain embodiments, the immunogenic compositions can comprise a purified NABB associated with at least one membrane protein containing a native conformational epitope, wherein the membrane protein does not contain the native conformational epitope when present in a detergent solubilized form. In certain embodiments, the membrane protein is an integral or peripheral membrane protein. An integral membrane protein can be selected from the group consisting of a Type I integral membrane protein, a Type II integral membrane protein, a seven transmembrane domain (7-TM) integral membrane protein, a G-protein coupled receptor, an ion-channel, and an ion-pump. In other embodiments, the membrane protein can be a chemokine receptor, a cytokine receptor, a receptor kinase, a receptor phosphatase, a receptor involved in cell-cell interactions, and a cellular adhesion molecule. In certain embodiments, the chemokine receptor interacts with chemokine subfamilies XC (XCR1), CXC (CXCR 1-7), CX3C (CX3CR 1), CC (CCR 1-9, GPR 2). In certain embodiments, the composition can further comprise a supplementary adjuvant. In these embodiments, the supplementary adjuvant can be alum, detoxified lipid A, a muramyl peptide, a saponin, a T-helper (Th) peptide, or a combination thereof.

BRIEF DESCRIPTION OF THE DRAWINGS

FIG. 1 is an amino acid sequence alignment of Zebrafish apolipoprotein A-1 (SEQ ID NO:1) and Human apolipoprotein A-1 (SEQ ID NO:2). The MGHHHHHH hexa-histidine (SEQ ID NO:25), LEVLFQGP Precission protease cleavage (SEQ ID NO:26), and IEGR Factor Xa protease cleavage (SEQ ID NO:27) sequences are also shown.

FIG. 2 shows the characterization of lipoprotein particles formed by Zebrafish apo A-1 with various POPC.

FIG. 3 shows the characterization of rho incorporated into NABB.

FIG. 4 shows visualization and stoichiometry of rho incorporated into NABB.

FIG. 5 shows the biochemical characterization of rho incorporated into NABB.

FIG. 6 shows gel-filtration of CCR5 incorporation into NABB.

FIG. 7 is a schematic of the Sandwich-ELISA Assay for characterizing CCR5-NABB.

FIG. 8 shows ligand mediated activation of CCR5-NABB.

DETAILED DESCRIPTION

Definitions

The term "agent", when used herein the context of a molecule associated with an NABB, refers herein to either a membrane protein or a hydrophobic molecule. The phrase "hydrophobic compound" as used herein refers to any compound that is capable of associating with lipid bilayer of an NABB.

The terms "polypeptide," "peptide" and "protein" are used interchangeably herein to refer to a polymer of amino acid residues of any length.

The term "lipid anchor" as used herein refers to any covalently linked hydrophobic moiety that provides for association of a protein with a phospholipid bilayer. Lipid anchors thus include, but are not limited to, those provided by palmitylation, myristoylation, prenylation, and addition of glycosylphosphatidylinositol anchors to a protein.

The term "label" as used herein refers to a detectable compound or composition that is conjugated directly or indirectly to the molecule being labeled. The label may be detectable by itself, for example, radioisotope labels or fluorescent labels, or may catalyze chemical alteration of a substrate compound or composition that is detectable, for example an enzymatic label.

The term "membrane protein", as used herein, includes any protein that can be associated with a membrane.

The term "immune response" as used herein refers to the ability to induce the production of an antibody against an antigenic epitope possessed a native or naturally occurring protein.

The term "vertebrate" as used herein refers to any animal classified as a vertebrate. For example, vertebrate includes, but is not limited to, humans, monkeys, cattle, goats, rabbits, mice, chickens, etc.

As used herein, the phrases "Zebrafish apolipoprotein A-I" or "Zebrafish apolipoprotein A-I variants" or the term "Zap 1" refer to an apolipoprotein A-I obtained or derived from Zebrafish (*Danio rerio*) that is capable of forming a nanoscale apolipoprotein bound phospholipid bilayer (NABB).

Apolipoprotein A-I Molecules

A variety of apolipoprotein A-I molecules can be used in the methods and compositions provided herein. In certain embodiments, apolipoprotein A-I molecules derived from vertebrates can be used. Such vertebrate apolipoprotein A-I molecules include, but are not limited to, those obtained or derived from human, equine, bovine, or piscine sources. Compositions and methods wherein N-terminally truncated derivatives of such vertebrate apolipoprotein A-I molecules are present or used are also contemplated. In certain embodiments, use of a Zebrafish apolipoprotein A-I or Zap 1 protein is contemplated. Zebrafish apolipoprotein A-I or Zap 1 molecules that can be used include, but are not limited to, a wild-type Zebrafish apolipoprotein A1 (SEQ ID NO:1), a Gln25Cys variant of a mature wild-type Zebrafish apolipoprotein A-I, and labeled derivatives thereof. Other Zebrafish apolipoprotein A-I or Zap 1 proteins that can be used include, but are not limited to, N-terminally truncated derivatives of; i) a wild-type Zebrafish apolipoprotein A-I (SEQ ID NO:1); ii) a Gln25Cys variant of a mature wild-type Zebrafish apolipoprotein A-I (SEQ ID NO:3); or labeled derivatives thereof. Also provided are naturally occurring and genetically engineered variants of Zebrafish apolipoprotein A1 molecules. Zebrafish apolipoprotein A-1 proteins that can be used thus include, but are not limited to, SEQ ID NO: 1, 3, 7, 8, and 9.

In certain embodiments, naturally occurring and genetically engineered variants of Zebrafish apolipoprotein A1 molecules can be used. Such Zebrafish apolipoprotein A1 variants include, but are not limited to, variants comprising conservative or non-conservative amino acid substitutions of SEQ ID NO:1 that can form a nanoscale apolipoprotein bound phospholipid bilayers (NABBs). Other Zebrafish apolipoprotein A1 variants that can be used include, but are not limited to, variants comprising sequences with at least 70%, 80%, 90%, 95%, or 99% sequence identity to SEQ ID NO:1 that can form a nanoscale apolipoprotein bound phospholipid bilayers (NABBs).

It has been determined herein that Zebrafish apolipoprotein A1 molecules are particularly useful for obtaining NABBs. Without seeking to be limited by theory, certain structural features of Zebrafish apolipoprotein A1 may provide for improved NABB formation activity. In this regard, amino acid sequence analysis shows that invariant proline residues occur every 22 or 11 amino acids in Zebrafish apolipoprotein A-I, suggesting that the length of Zebrafish apolipoprotein A-I can be divided into tandem 22/11-mer helices which interact with the lipid side chains. The tandem 22/11-mer helices are punctuated by proline 'hinges', similar to the hypothesized lipid-binding mechanism of human apo A-I. Amino acid sequence comparison between Zebrafish apo A-1 and Human apo A-1 shows a general conservation of the chemical type of the amino acid residue in Zebrafish apolipoprotein A-I at the corresponding positions of the human apolipoprotein A-I. The sequence similarity points to a similar lipid binding mechanism and amphipathicity of Zebrafish apolipoprotein A-I compared with human apolipoprotein A-I. C-terminal residues may not be as important for lipid binding in Zebrafish apolipoprotein A-I compared with human apolipoprotein A-I as determined by hydropathy analysis. N-terminal tails of both Zebrafish and human apolipoprotein A-I show a conserved pattern of high hydrophobicity, which may indicate a possible role of the N-terminal residues of Zebrafish apolipoprotein A-I in lipid binding. Notably, Zebrafish apolipoprotein A-I contains a proline at position 186 which is the region between putative helices 7 and 8, whereas human apo A-1 lacks a corresponding proline at the same position. Zebrafish apo A-1 also exhibited a more regular pattern of negative peaks (favorable salt bridges) in the score throughout the length of its helix compared with human apo A-I according to analysis using the ALIGN program to calculate the weighted number of salt bridges and like charge appositions for each docking position (Segrest et al. *J. Biol. Chem.* 274, 31755-31758 (1999)). This may point to a mechanism in Zebrafish apo A-I where multiple possible helical registries are possible, as opposed to one particular more favorable registry as with human apolipoprotein A-I. By not constraining the relative orientations (helix registers) of the apo A-I helices, Zebrafish apolipoprotein A-I may be able to form discoidal lipid particles rapidly. The particles formed by Zebrafish apolipoprotein A-I may also be more resistant to dilution compared with human apolipoprotein A-I since the Zebrafish apolipoprotein A-I helices will be able to dock in multiple orientations in an equilibrium between lipid-bound and lipid-free states at high dilutions.

In this regard, apolipoprotein A-I proteins from other piscine sources (i.e. fish) other than Zebrafish can also be used in the methods described herein. Such piscine apolipoprotein A-1 proteins include, but are not limited to, •apolipoprotein A-1 proteins from eel (*Anguilla japonica*: GI:76573852, SEQ ID NO:10; GI:13591600, SEQ ID NO:11), carp (*Cyprinus carpio*: GI:13445027, SEQ ID NO:12), trout (*Oncorhynchus mykiss*: GI:185132771, SEQ ID NO:13; GI:2791881, SEQ ID NO:14; GI:2791883, SEQ ID NO:15), sea-bass (*Morone saxatilis*: GI:199584171, SEQ ID NO:16; GI:199584169, SEQ ID NO:17; GI:199584167, SEQ ID NO:18), cod (*Gadus morrhua*: GI:52783666; SEQ ID NO:19), salmon (*Salmo salar*, GI:185132488, SEQ ID NO:20; GI:213512936, SEQ ID NO:21; GI:209734648, SEQ ID NO:22), and pufferfish (*Takifugu rubripes*: GI:118344628, SEQ ID NO:23; GI:57157761, SEQ ID NO:24). Apolipoprotein A-1 proteins from eel, *Anguilla japonica*: GI:76573852, SEQ ID NO:10; GI:13591600 (SEQ ID NO:11) can be used in certain preferred embodiments.

In other embodiments, the Zebrafish apolipoprotein A1 variant can thus comprise an apolipoprotein derived from another species where key amino acid residues in particular regions or positions of that apolipoprotein are substituted with the corresponding residues found in those regions or positions of the Zebrafish apolipoprotein. In certain exemplary embodiments, a proline at position 186, which is in the region between putative helices 7 and 8, is substituted into the corresponding position of an apolipoprotein that lacks a corresponding proline at that same position. Amino acid substitutions in an apolipoprotein A1 derived from a species other than Zebrafish that provide for a more regular pattern of negative peaks (favorable salt bridges) in the ALIGN program score throughout the length of a helix as is characteristic of Zebrafish apolipoprotein A1 are also provided herein. Apolipoprotein A1 proteins that can be substituted with the corresponding residues from a Zebrafish apolipoprotein A1 to obtain a Zebrafish apolipoprotein A-I variant include, but are not limited to, human, bovine, and equine apolipoprotein A-I. Apolipoprotein A1 proteins that can be substituted with the corresponding residues from a Zebrafish apolipoprotein A1 to obtain a Zebrafish apolipoprotein A-I variant also include, but are not limited to, fish (piscine) apolipoprotein A-1 proteins comprising any of SEQ ID NO: 10-24. Apolipoprotein A1 proteins that can be substituted with the corresponding residues from apolipoprotein A-1 proteins from eel, *Anguilla japonica*: GI:76573852, SEQ ID NO:10; GI:13591600 (SEQ ID NO:11) in certain preferred embodiments.

Also provided herein are Zebrafish apolipoprotein A-I proteins, or variants thereof, that comprise N-terminal affinity purification tags, C-terminal affinity purification tags, detectable labels, and combinations thereof. In certain embodiments, the affinity purification tag can be a removable tag. In certain embodiments, the label can be incorporated at a Cys residue substituted at a position corresponding to residue 25 of SEQ ID NO:1.

Method for Obtaining a Nanoscale Apolipoprotein Bound Phospholipid Bilayer (NABB) Associated with an Agent Methods that provide for rapid recovery of nanoscale apolipoprotein bound phospholipid bilayers (NABB) associated with at least one agent are provided herein. The advantages of these methods over previously disclosed methods include more rapid recovery of NABBs associated with an agent, increased activity of membrane protein agents associated with NABBs, and/or retention of native conformational epitopes in membrane protein agents associated with NABBs. Other advantages of methods provided herein include recovery of homogenous populations of NABB with defined numbers of associated membrane proteins per NABB particle and defined lipid compositions.

Methods provided herein can first comprise obtaining a mixture comprising an apolipoprotein A-I, one or more phospholipid(s), one or more agent(s), and one or more detergent(s), wherein the mixture is substantially deficient in NABB. The detergent(s) is depleted from the mixture within about one hour of obtaining the mixture to obtain a detergent depleted mixture comprising a NABB associated with at least one agent. The NABB associated with at least one agent from the detergent depleted mixture can then be purified.

The mixture comprising an apolipoprotein A-I, one or more phospholipid(s), one or more distinct agent(s), and one or more detergent(s) that is substantially deficient in NABB can be obtained by providing detergent(s) at a concentration that precludes NABB formation. However, the detergent concentration can be adjusted so as to maintain membrane protein activity and/or conformation while still precluding NABB formation. Such mixtures can be obtained at temperatures of about 2° C. to about 30° C. Lipids and detergents can be selected based on their solubility at a desired mixture temperature. In certain embodiments, detergents with comparatively low CMC (Critical Micelle Concentration) values can be used.

In certain embodiments, Zebrafish apolipoprotein A1 or a variant thereof is used in the mixture.

In certain embodiments, rapid removal of detergents (i.e. within about one hour of obtaining the mixture) can be effected by hydrophobic adsorption chromatography. Thus, in certain embodiments, detergent(s) is depleted from the mixture within about one hour of obtaining the mixture. In other embodiments, detergent(s) is depleted from the mixture within about thirty (30) minutes of obtaining the mixture. The use of hydrophobic adsorption chromatography (i.e. detergent removing gels) also provides for removal of detergents with comparatively low CMC (Critical Micelle Concentration) values. In certain embodiments, detergent(s) with CMC values of about 50 mM or less at a temperature of about 20 to 25 degrees centigrade can be used. In contrast to hydrophobic adsorption chromatography methods that provide for rapid removal of detergents with low CMC values, dialysis-mediated detergent depletion is only effective for removing detergents with relatively high CMC values.

Detergents can be rapidly depleted by either column or batch chromatography that uses resins or gels suitable for hydrophobic adsorption chromatography. Hydrophobic chromatography resins that can be used include, but are not limited to, Extracti Gel D (Pierce Biotechnology, Rockford Ill.), CALBIOSORB™ (Calbiochem, San Diego, Calif.), SDR HyperD™ Solvent-Detergent Removal Chromatography Resin (PALL Corporation, Ann Arbor, Mich.). A detergent deficient mixture comprising the NABB can be obtained by washing the resin with a suitable detergent-free buffer.

Purifying the NABB associated with at least one agent from the detergent depleted mixture can be accomplished by gel-filtration chromatography or other size exclusion methods. Examples of gel-filtration media include, but are not limited to, Sephacryl, Superdex, Superose, Superose series, or Superose 6 10/30, Affinity and/or immuno-affinity based purification methods can also be used either exclusively or in conjunction with size exclusion methods to effect purification of the NABB associated with just one membrane protein. Membrane proteins can in certain embodiments further comprise affinity purification tags that provide for purification. Such tags include, but are not limited to, peptide sequences that are recognized by immobilized antibodies or that recognize immobilized ligands. In certain embodiments, an affinity tag can be linked to the membrane protein via a cleavable or labile linkage that further facilitates purification. Such cleavable linkages include, but are not limited to, protease cleavage recognition sites. Alternatively, the apolipoprotein itself can comprise any of the aforementioned affinity purification tags that provide for purification. In certain embodiments, Zebrafish apolipoprotein A-I or a variants thereof comprising either N- or C-terminal affinity tags can be used. In certain embodiments, Zebrafish apolipoprotein A1 or a variants thereof comprising an N-terminal hexahistidine tag can be used.

In certain embodiments, the agent is a membrane protein. Membrane proteins include, but are not limited to, proteins that are associated with membranes in their naturally occurring state and proteins that are modified to provide for membrane association. Modifications that provide for membrane association include, but are not limited to, recombinant DNA-mediated modifications that add one or more peptide sequences that provide for membrane association. Peptide sequences that provide for membrane association can include, but are not limited to, trans-membrane domains and/or sequences that provide for addition of a lipid anchor. Chemically-mediated modifications to a protein can also provide for membrane association. Membrane proteins used in the methods and compositions provided herein can thus include proteins that are not associated with membranes in their naturally occurring state but that have been modified to provide from membrane association.

In certain embodiments, the agent can be a membrane protein that is an integral membrane protein. Integral membrane proteins used include, but are not limited to, Type I integral membrane proteins, a Type II integral membrane proteins, a seven transmembrane domain (7-TM) integral membrane proteins, ion-channels, and ion-transporters. In other embodiments, the membrane protein is a peripheral membrane protein. In certain embodiments where the membrane protein is a peripheral membrane protein, the peripheral membrane protein can be associated with the NABB by a lipid anchor. Seven transmembrane domain (7-TM) integral membrane proteins that can be used include, but are not limited, to G-Protein Coupled Receptors (GPCRs). Such GPCRs can be either those characterized by binding to a ligand or orphan GPCRs for which a binding ligand has yet to be identified. GPCRs that bind ligands including, but not limited to, amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and LPA. In other embodiments, the membrane protein can be a member of the cytochrome P450 family. Membrane proteins that can be used in the methods and compositions include, but are not limited to, chemokine receptors, cytokine receptors, receptor kinases, receptor phosphatases, receptors involved in cell-cell interactions, and cellular adhesion molecules. In certain embodiments, CCR5 receptors and variants thereof can be used. CCR5 receptor variants used include, but are not limited to, CCR5 variants deficient in glycosylation, tyrosine sulfation, or a combination thereof. In still other embodiments a combination of integral and peripheral membrane proteins can be used.

In certain embodiments the agent can be a hydrophobic compound. Hydrophobic compounds used can include, but are not limited to, compounds that are wholly hydrophobic as well as compounds that comprise hydrophobic moieties that provide for association with an NABB. Thus, compounds comprising both hydrophilic and hydrophobic moieties can be used where the hydrophobic moiety provides for association with the NABB. NABBs associated with hydrophobic compounds can thus be used for encapsulation and/or delivery of hydrophobic agents of pharmaceutical, therapeutic, or diagnostic value. Such pharmaceutical or therapeutic agents can include, but are not limited to, antibacterial, antiviral, antifungal, anticancer, immunosuppressive, anesthetic, psychotropic agents, or vitamins. Therapeutic or pharmaceutical hydrophobic compounds associated with the NABB can include, but are not limited to, amphotericin, miconazole, paclitaxel, taxol, doxorubicin, cyclosporine, nelfinavir, propofol, diazepam, retinal, retinol, retinoic acid, phytonadione, or a derivative thereof.

Various fluorescent markers can be used to label membrane proteins. Commercially available maleimide-linked fluorophores are particularly useful for site-specific labeling of membrane proteins having cysteine side chains. Fluorophore maleimides that can be used for labeling include, but are not limited to, fluorescein, Alexa-488, Cy3, tetramethyl-rhodamine, Alexa-546, Alexa-594, Alexa-647, Cy5 and Atto-655. Alexa-546 led to the most efficient labeling of rhodopsin in terms of lowest dye excess required to achieve stoichiometric labeling (1:1 Dye:Rho). Atto-655 also exhibited efficient labeling of rhodopsin and may be an ideal fluorophore in the long-wavelength region to label rhodopsin. Stoichiometric labeling was achieved with a 3-times molar excess of Atto-655 over rho, and two cysteines (Cys 316 and Cys 140) could be modified by doubling the initial dye excess (9-fold molar excess over rhodopsin).

Membrane proteins can also be labeled for electron microscopy. Gold reagents can be used to label membrane proteins for electron microscopy. Gold reagents including, but not limited to, Nanogold® (Nanoprobes, NY), Undecagold, and colloidal gold reagents can be used. Preferably, Nanogold® reagent is used.

Any phospholipid or phospholipid mixture that provides for bilayer formation and that is compatible with apolipoprotein A-I and the desired membrane protein can be used. In certain embodiments, such phospholipids can comprise a 6 to 20 carbon saturated or unsaturated fatty acid chain and a head group. Head groups include, but are not limited to, positively charged, negatively charged, zwitterionic, or uncharged head groups. Exemplary head groups include, but are not limited to, phosphatidyl choline, phosphatidyl ethanolamine, and phosphatidyl serine. Phospholipids that can be used include, but are not limited to, 1-Palmitoyl-2-Oleoyl-sn-Glycero-3-Phosphocholine (POPC), 1,2-Dimyristoyl-sn-Glycero-3-Phosphocholine (DMPC), 1,2-Dioleoyl Phosphatidylethanolamine (DOPE), 1,2-Dipalmitoyl-sn-Glycero-3-Phosphoethanolamine (DPPE), 1,2-Dioleoyl Phosphatidylcholine (DOPC), 1,2-Dioleoyl Phosphatidylserine (DOPS), labelled derivatives thereof, or a combination thereof.

Any detergent that provides for inhibition of bilayer formation and that is compatible with apolipoprotein A-I and the desired agent can be used. Detergents that can be used include, but are not limited to, sodium cholate, n-octyl-beta-D-glucopyranoside (OG), n-dodecyl-beta-D-maltopyranoside (DDM), 5-Cyclohexylpentyl beta-D-maltopyranoside (Cymal-5), 3-[(3-Cholamidopropyl)dimethylammonio]-1-propanesulfonate (CHAPS), or a combination thereof. In certain embodiments, methods provided herein permit use of detergents with CMC values of about 50 mM or less at a temperature of about 20 to 25 degrees centigrade. In certain embodiments, the detergent comprises at least one of FOS-CHOLINE, FOS-MEA, CYFOS, FENFOS, FOSFEN, a sugar-based detergent, a polyoxyethylene based detergent, a bile-salt based detergent, or a combination thereof. A sugar based detergent can include, but is not limited to, n-octyl-beta-D-glucopyranoside (OG), n-nonyl-beta-D-glucopyranoside, n-dodecyl-beta-D-maltopyranoside (DDM), 5-Cyclohexylpentyl beta-D-maltopyranoside (Cymal-5). A bile-salt based detergent can include, but is not limited to, sodium cholate, 3-[(3-Cholamidopropyl)dimethylammonio]-1-propane sulfonate (CHAPS), 3-[(3-Cholamidopropyl)dimethylammonio]-2-hydroxy-1-propane sulfonate (CHAPSO), or a derivative thereof. A polyoxyethylene based detergent can include, but is not limited to, Tween 20, Triton X-100, or a derivative thereof.

Various fluorescent markers can be used to label the phospholipid(s) used in the method. In certain embodiments, the fluorescent phospholipid is provided as a mixture with unlabelled phospholipids. Typically, such labelled phospholipids would be included at a ratio that would provide for at least one labelled phospholipid per NABB. In certain embodiments, a ratio of about 1 part labelled phospholipid to about 100 parts unlabelled phospholipid can be used (volume/volume ratio). In other embodiments, a ratio of about 1 part labelled phospholipid to about 50 parts unlabelled phospholipid can be used. In other embodiments, a ratio of about 1 part labelled phospholipid to about 25 parts unlabelled phospholipid can be used. Fluorescent labels for phospholipids that can be used include, but are not limited to, BODIPY, diphenylhexatriene propionic acid, nitrobenzoxadiazole (NBD), Lissamine rhodamine B (LRB), pyrene, Dansyl, Marina Blue, Pacific Blue, Oregon Green, and Texas Red (Invitrogen, Carlsbad, Calif.).

The phospholipid(s) and apolipoprotein A-I can be used at molar ratios of about 25:1 phospholipid(s):apolipoprotein A-I to about 200:1 phospholipid(s):apolipoprotein A-I for obtaining a mixture comprising a apolipoprotein A-I, one or more phospholipid(s), and one or more detergent(s) that is substantially deficient in NABB. In certain embodiments a phospholipid(s):apolipoprotein A-I molar ratio of about 50:1 phospholipid(s):apolipoprotein A-I to about 160:1 phospholipid(s):apolipoprotein A-I is preferred. In certain embodiments a phospholipid:apolipoprotein A-I molar ratio of about 50:1 phospholipid(s):apolipoprotein A-I is preferred. In other embodiments a phospholipid:apolipoprotein A-I molar ratio of about 75:1 phospholipid(s):apolipoprotein A-I is preferred. In still other embodiments a phospholipid:apolipoprotein A-I phospholipid(s):apolipoprotein A-I molar ratio of about 100:1 phospholipid(s):apolipoprotein A-I is preferred. In yet other embodiments a phospholipid(s):apolipoprotein A-I molar ratio of about 160:1 phospholipid(s):apolipoprotein A-I is preferred. In certain embodiments, Zebrafish apolipoprotein A-I or a variant thereof is used in the mixture.

In certain embodiments, the phospholipid(s):apolipoprotein A-I:membrane protein ratio used to obtain a mixture comprising an apolipoprotein A-I, one or more phospholipid(s), one or more distinct membrane protein(s), and one or more detergent(s) provides for a substantially homogeneous population of purified NABB wherein at least 70% of the NABB are associated with one membrane protein. In other embodiments, the phospholipid:apolipoprotein A-I:membrane protein ratio used to obtain a mixture comprising a apolipoprotein A-I, one or more phospholipid(s), one or more distinct membrane protein(s), and one or more detergent(s), wherein the mixture is substantially deficient in NABB provides for a substantially homogeneous population of purified NABB wherein at least 70% of the NABB are associated with two membrane proteins. When used herein in this context, the phrase "substantially homogeneous population" refers to a population where the indicated percentage of NABB in the population are of about the same diameters and contain the same number of associated membrane proteins. In certain embodiments, at least 80%, 90%, or 95% of the NABB in the substantially homogenous population contain the same number of associated membrane proteins. As the phospholipid(s) used in the mixture can be provided in a purified form, it is further anticipated that the phospholipid composition of the NABBs in the population will be relatively constant. Those skilled in the art will also appreciate that such ratios can be empirically determined by systematically varying the ratio of phospholipid(s) to apolipoprotein A-I and membrane protein in the mixture, obtaining the purified NABB associated with membrane proteins, and quantifying the number of membrane proteins per NABB obtained. The number of membrane proteins per NABB can be determined by electron microscopy imaging of labelled NABB or other suitable techniques. In certain embodiments, Zebrafish apolipoprotein A-I or a variant thereof is used in the mixture.

In another aspect of the invention, an activity of the membrane protein associated with the purified NABB is increased relative to the activity of the membrane protein associated with an NABB that is obtained by dialysis-mediated detergent depletion. Activities of an NABB-associated membrane protein that can be increased by methods provided herein include, but are not limited to, a ligand binding, a transport, a channel, or a enzymatic activity. Without seeking to be limited by theory, such increases in activity may result from the more rapid depletion of detergent that is provided by the methods of this invention. Increases in activity of the membrane protein associated with the purified NABB of at least 50% relative to the activity of the membrane protein associated with an NABB that is obtained by dialysis-mediated detergent depletion can be obtained using methods provided herein.

In another aspect of the invention, a substantially homogenous population of nanoscale apolipoprotein bound phospholipid bilayers associated with at least one membrane protein are purified. In certain embodiments, the population comprises at least 70% NABB that are associated with one membrane protein. In other embodiments, the population comprises at least 70% NABB that are associated with two membrane proteins. In certain embodiments, at least 80%, 90%, or 95% of the NABB in the substantially homogenous population contain the same number of associated membrane proteins. Purification of such NABB can be effected using size exclusion chromatography, affinity chromatography, or combinations thereof.

Method for Obtaining NABB without Associated Membrane Proteins

Methods for obtaining NABB that are not associated with a membrane protein are also provided herein. NABB that are not associated with a membrane protein are useful in a variety of biochemical assays. NABB that are not associated with a membrane protein can also be combined with hydrophobic compounds to obtain compositions useful for therapeutic, pharmaceutical, or diagnostic purposes. Thus, another aspect of the invention is a method for obtaining NABBs comprising obtaining a mixture comprising an apolipoprotein A-I, one or more phospholipid(s), and one or more detergents, wherein the mixture is substantially deficient in NABB molecules; depleting the detergent from the mixture to obtain a detergent depleted mixture comprising a nanoscale apolipoprotein bound phospholipid bilayer, wherein the detergent is depleted from the mixture within about one hour of obtaining the mixture comprising an apolipoprotein A-I, one or more phospholipid(s), and one or more detergents; and, purifying the nanoscale apolipoprotein bound phospholipid bilayer from the detergent depleted mixture. In certain embodiments, Zebrafish apolipoprotein A-I or a variant thereof is used in the mixture. In certain embodiments, a Zebrafish apolipoprotein A-I variant comprising sequence with at least 70%, 80%, 90%, 95%, or 99% sequence identity to SEQ ID NO:1 is used. In certain embodiments, a Zebrafish apolipoprotein A-I variant comprising a Gln25Cys mutation is used. Such a Zebrafish apolipoprotein A-I variants comprising a Gln25Cys mutation may further comprise a labeling group that is covalently linked to the cysteine residue at position 1.

In general, these methods parallel the methods provided herein for obtaining NABBs with associated membrane proteins with the exception that the membrane protein is omitted from the detergent containing mixture that comprises an apolipoprotein A-I and detergent. Another difference is that purification of the NABBs that lack associated membrane proteins can not be effected with an affinity based purification method using an affinity labelled membrane protein. However, affinity purification based on affinity labelled apolipoprotein A-I proteins can be used to purify the NABB produced by the methods provided herein. Thus, apolipoprotein A-I proteins comprising tags that include, but are not limited to, peptide sequences that are recognized by immobilized antibodies or that recognize immobilized ligands can be used. In certain embodiments, an affinity tag can be linked to the apolipoprotein A-I proteins via a cleavable or labile linkage that further facilitates purification. Such cleavable linkages include, but are not limited to, protease cleavage recognition sites. In certain embodiments, Zebrafish apolipoprotein A-I or a variants thereof comprising either N- or C-terminal affinity tags can be used. In certain embodiments, Zebrafish apolipoprotein A-I or a variants thereof comprising an N-terminal hexahistidine tag can be used.

The mixture comprising an apolipoprotein A-I, one or more phospholipid(s), and one or more detergent(s) that is substantially deficient in NABB can be obtained by providing detergent(s) at a concentration that precludes NABB formation. Such mixtures can be obtained at temperatures of about 2° C. to about 30° C. Lipids and detergents can be selected based on their solubility at a desired mixture temperature. In certain embodiments, detergents with comparatively low CMC (Critical Micelle Concentration) values can be used. In certain embodiments, Zebrafish apolipoprotein A-I or a variant thereof is used in the mixture.

In certain embodiments, rapid removal of detergents (i.e. within about one hour of obtaining the mixture) can be effected by hydrophobic adsorption chromatography. Thus, in certain embodiments, detergent(s) is/are depleted from the mixture within about one hour of obtaining the mixture. In other embodiments, detergent(s) is/are depleted from the mixture within about thirty (30) minutes of obtaining the mixture. The use of hydrophobic adsorption chromatography (i.e. detergent removing gels) also provides for removal of detergents with comparatively low CMC (Critical Micelle Concentration) values. In certain embodiments, detergent(s) with CMC values of about 50 mM or less at a temperature of about 20 to 25 degrees centigrade can be used. In contrast to hydrophobic adsorption chromatography methods that provide for rapid removal of detergents with low CMC values, dialysis-mediated detergent depletion is only effective for removing detergents with relatively high CMC values.

Detergents can be rapidly depleted by either column or batch chromatography that uses resins or gels suitable for hydrophobic adsorption chromatography. Hydrophobic chromatography resins that can be used include, but are not limited to, Extracti Gel D (Pierce Biotechnology, Rockford Ill.), CALBIOSORB™ (Calbiochem, San Diego, Calif.), SDR HyperD™ Solvent-Detergent Removal Chromatography Resin (PALL Corporation, Ann Arbor, Mich.). A detergent deficient mixture comprising the NABB can be obtained by washing the resin with a suitable detergent-free buffer.

Any phospholipid or phospholipid mixture that provides for bilayer formation and that is compatible with apolipoprotein A-I can be used. In certain embodiments, such phospholipids can comprise a 6 to 20 carbon saturated or unsaturated fatty acid chain and a head group. Head groups include, but are not limited to, positively charged, negatively charged, zwitterionic, or uncharged head groups. Exemplary head groups include, but are not limited to, phosphatidyl choline, phosphatidyl ethanolamine, and phosphatidyl serine. Phospholipids that can be used include, but are not limited to, 1-Palmitoyl-2-Oleoyl-sn-Glycero-3-Phosphocholine (POPC), 1,2-Dimyristoyl-sn-Glycero-3-Phosphocholine (DMPC), 1,2-Dioleoyl Phosphatidylethanolamine (DOPE), 1,2-Dipalmitoyl-sn-Glycero-3-Phosphoethanolamine (DPPE), 1,2-Dioleoyl Phosphatidylcholine (DOPC), 1,2-Dioleoyl Phosphatidylserine (DOPS), labelled derivatives thereof, or a combination thereof.

Any detergent that provides for inhibition of bilayer formation and that is compatible with apolipoprotein A-I can be used. Detergents that can be used include, but are not limited to, sodium cholate, n-octyl-beta-D-glucopyranoside (OG), n-dodecyl-beta-D-maltopyranoside (DDM), 5-Cyclohexylpentyl beta-D-maltopyranoside (Cymal-5), 3-[(3-Cholamidopropyl)dimethylammonio]-1-propanesulfonate (CHAPS), or a combination thereof. In certain embodiments, methods provided herein permit use of detergents with CMC values of about 50 mM or less at a temperature of about 20 to 25 degrees centigrade. In certain embodiments, the detergent comprises at least one of FOS-CHOLINE, FOS-MEA, CYFOS, FENFOS, FOSFEN, a sugar-based detergent, a polyoxyethylene based detergent, a bile-salt based detergent, or a combination thereof. A sugar based detergent can include, but is not limited to, n-octyl-beta-D-glucopyranoside (OG), n-nonyl-beta-D-glucopyranoside, n-dodecyl-beta-D-maltopyranoside (DDM), 5-Cyclohexylpentyl beta-D-maltopyranoside (Cymal-5). A bile-salt based detergent can include, but is not limited to, sodium cholate, 3-[(3-Cholamidopropyl)dimethylammonio]-1-propane sulfonate (CHAPS), 3-[(3-Cholamidopropyl)dimethylammonio]-2-hydroxy-1-propane sulfonate (CHAPSO), or a derivative thereof. A polyoxyethylene based detergent can include, but is not limited to, Tween 20, Triton X-100, or a derivative thereof.

Various fluorescent markers can be used to label the phospholipid(s) used in the method. In certain embodiments, the fluorescent phospholipid is provided as a mixture with unlabelled phospholipids. Typically, such labelled phospholipids would be included at a ratio that would provide for at least one labelled phospholipid per NABB. In certain embodiments, a ratio of about 1 part labelled phospholipid to about 100 parts unlabelled phospholipid can be used (volume/volume ratio). In other embodiments, a ratio of about 1 part labelled phospholipid to about 50 parts unlabelled phospholipid can be used. In other embodiments, a ratio of about 1 part labelled phospholipid to about 25 parts unlabelled phospholipid can be used. Fluorescent labels for phospholipids that can be used include, but are not limited to, BODIPY, diphenylhexatriene propionic acid, nitrobenzoxadiazole (NBD), Lissamine rhodamine B (LRB), pyrene, Dansyl, Marina Blue, Pacific Blue, Oregon Green, and Texas Red (Invitrogen, Carlsbad, Calif.).

The phospholipid(s) and apolipoprotein A-I can be used at molar ratios of about 25:1 phospholipid(s):apolipoprotein A-I to about 200:1 phospholipid(s):apolipoprotein A-I for obtaining a mixture comprising a apolipoprotein A-I, one or more phospholipid(s), and one or more detergent(s) that is substantially deficient in NABB. In certain embodiments a phospholipid(s):apolipoprotein A-I molar ratio of about 50:1 phospholipid(s):apolipoprotein A-I to about 160:1 phospholipid(s):apolipoprotein A-I is preferred. In certain embodiments a phospholipid:apolipoprotein A-I molar ratio of about 50:1 phospholipid(s):apolipoprotein A-I is preferred. In other embodiments a phospholipid:apolipoprotein A-I molar ratio of about 75:1 phospholipid(s):apolipoprotein A-I is preferred. In still other embodiments a phospholipid:apolipoprotein A-I phospholipid(s):apolipoprotein A-I molar ratio of about 100:1 phospholipid(s):apolipoprotein A-I is preferred. In yet other embodiments a phospholipid:apolipoprotein A-I molar ratio of about 160:1 phospholipid(s):apolipoprotein A-I is preferred. In certain embodiments, Zebrafish apolipoprotein A-I or a variant thereof is used in the mixture.

In another aspect of the invention, a substantially homogenous population of nanoscale apolipoprotein bound phospholipid bilayers are purified. When used herein in this context, the phrase "substantially homogeneous population" refers to a population where the indicated percentage of NABB in the population are of about the same diameters. In certain embodiments, the homogenous population comprises NABBs with a diameter of about 9 nm to about 17 nm or with a diameter of about 10 nm to about 17 nm. In certain embodiments, the population comprises at least 70% NABB of a single diameter. A NABB diameter can be determined by methods that include, but are not limited to, determination of a Stokes diameter by chromatography or by analysis of electron micrographs. In certain embodiments, at least 85%, 90%, or 95% of the NABB in the substantially homogenous population are of a single diameter. In certain embodiments, the homogenous population comprises NABBs with a single Stokes diameter of about 10, 11.6, or 12.5 nm. In other embodiments, the population comprises at least 70% NABB with a single Stokes diameter of about 17 nm are obtained. As used herein, specific Stokes' diameter values of 10, 11.6, 12.5 nm, or 17 nm refer to values obtained by gel filtration chromatography on a calibrated a Superose 6 10/30 column.

To obtain substantially homogeneous populations of NABB of a single diameter, the ratio of phospholipid to apolipoprotein A-I can be adjusted to provide for NABBs of a desired diameter. Those skilled in the art will also appreciate that such ratios can be empirically determined by systematically varying the ratio of phospholipid(s) to apolipoprotein A-I in the mixture, obtaining the purified NABB, and determining the diameter of the NABB obtained. In certain embodiments, a ratio of about 75 parts 1-palmitoyl-2-oleoyl-sn-glycero-3-phosphocholine (POPC) to 1 part Zebrafish apolipoprotein A-I is used in the mixture to provide NABBs with a diameter of about 10-13 nm. In certain embodiments, a ratio of about 100 parts 1-palmitoyl-2-oleoyl-sn-glycero-3-phosphocholine (POPC) to 1 part Zebrafish apolipoprotein A-I; embodiments, Zebrafish apolipoprotein A-I or a variant thereof is used in the mixture to provide NABBs with a diameter of about 17 nm. In certain embodiments, Zebrafish apolipoprotein A-I that comprises SEQ ID NO:1 is used in the mixture.

NABBs obtained by this method can also be combined with a hydrophobic compound to obtain an NABB associated with a hydrophobic compound. Any method of combining the NABBs and hydrophobic compound that provides for association of the hydrophobic compound with the NABBs can be used. Methods of combining include, but are not limited to, mixing an NABB preparation with a hydrophobic compound in a solution comprising a concentration of one or more solvent(s) that provides for solubilization of both the NABBs and the hydrophobic compound. Solvents that can be used for this purpose include, but are not limited to, ethanol, methanol, propanol, butanol and combinations thereof. Association of the hydrophobic compound with the NABB can be effected by methods including, but not limited to, vortexing and/or solvent removal. Once the hydrophobic compound is associated with the NABBs, unassociated compounds can be removed from the mixture by chromatographic methods.

Hydrophobic compounds used can include, but are not limited to, compounds that are wholly hydrophobic as well as compounds that comprise hydrophobic moieties that provide for association with an NABB. Thus, compounds comprising both hydrophilic and hydrophobic moieties can be used where the hydrophobic moiety provides for association with the NABB. NABBs associated with hydrophobic compounds can thus be used for encapsulation and/or delivery of hydrophobic agents of pharmaceutical, therapeutic, or diagnostic value. Such pharmaceutical or therapeutic agents can include, but are not limited to, antibacterial, antiviral, antifungal, anti-cancer, immunosuppressive, anesthetic, psychotropic agents, lipohilic vitamins, a glucocorticoid, a mineral corticoid or a hormone. Therapeutic or pharmaceutical hydrophobic compounds associated with the NABB can include, but are not limited to, amphotericin, miconazole, paclitaxel, taxol, doxorubicin, cyclosporine, nelfinavir, propofol, diazepam, retinal, retinol, retinoic acid, phytonadione, or a derivative thereof.

Methods for Obtaining NABBs Associated with an Agent from a Cell Membrane Protein Fraction Also provided herein are methods of obtaining NABBs associated with an agent derived from, or provided to, cells. Such cell-based methods can thus provide for the isolation of a membrane protein from a cell when the agent is a membrane protein. Such cell based methods can also provide for recovery of NABBs associated with a hydrophobic compound produced or provided to a cell when the agent is a hydrophobic compound. In general, these cell-based methods parallel the methods provided herein for obtaining NABBs with associated agents with the exception that the agent is provided in a cell membrane protein fraction obtained from cells. To obtain NABBs associated with an agent from cells, the cells comprising the agent are lysed to obtain a cell membrane protein fraction which is then combined with an apolipoprotein A-I to obtain a mixture that lacks or is substantially deficient in NABBs and comprises one or more phospholipid(s) and one or more detergent(s). In certain embodiments, detergent(s) and/or lipids and/or phospholipids present in the mixture comprising the cell membrane protein fraction and apolipoprotein A-I are exchanged with other detergents and/or phospholipids to obtain the mixture that is deficient in NABB and comprises one or more phospholipid(s) and one or more detergent(s). In other embodiments, apolipoprotein A-1 can simply be added directly to a cell membrane protein fraction that comprises phospholipids and detergent(s) to obtain the mixture that is deficient in NABB and comprises one or more phospholipid(s) and one or more detergent(s). Detergent is rapidly depleted from this mixture within about one hour as per the previously described methods to obtain a detergent depleted mixture comprising a NABB associated with at least one agent. These NABB associated with at least one agent are then purified as per the previously described methods for purification. In certain embodiments, a Zebrafish apolipoprotein A-I variant comprising sequence with at least 70%, 80%, 90%, 95%, or 99% sequence identity to SEQ ID NO:1 is used. In certain embodiments, a Zebrafish apolipoprotein A-I variant comprising a Gln25Cys mutation is used. Such a Zebrafish apolipoprotein A-I variants comprising a Gln25Cys mutation may further comprise a labeling group that is covalently linked to the cysteine residue at position 25. An exemplary Zebrafish apolipoprotein A-I variant comprising a Gln25Cys mutation is provided herein as SEQ ID NO:3.

Cell lysis can be achieved by using suitable buffer/detergent compositions that provide for retention of a native conformational epitope of a membrane protein. Such compositions can also comprise lipids or phospholipids. Phospholipids that can be used include, but are not limited to, 1-Palmitoyl-2-Oleoyl-sn-Glycero-3-Phosphocholine (POPC), 1,2-Dimyristoyl-sn-Glycero-3-Phosphocholine (DMPC), 1,2-Dioleoyl Phosphatidylethanolamine (DOPE), 1,2-Dipalmitoyl-sn-Glycero-3-Phosphoethanolamine (DPPE), 1,2-Dioleoyl Phosphatidylcholine (DOPC), 1,2-Dioleoyl Phosphatidylserine (DOPS), labelled derivatives thereof, or a combination thereof. Detergents that can be used include, but are not limited to, sodium cholate, n-octyl-beta-D-glucopyranoside (OG), n-dodecyl-beta-D-maltopyranoside (DDM), 5-Cyclohexylpentyl beta-D-maltopyranoside (Cymal-5), 3-[(3-Cholamidopropyl)dimethylammonio]-1-propanesulfonate (CHAPS), or a combination thereof. In certain embodiments, lysis can be achieved with a buffer comprising lipids and detergents reported to preserve CCR5 stability (Navratilova et al. *Anal. Biochem.* 339, 271-281 (2005); Navratilova et al. *Anal. Biochem.* 355, 132-139 (2006). An exemplary lysis buffer can thus comprise about 20 mM Tris (pH 7.0), about 0.1M $(NH_4)_2SO_4$, about 10% glycerol, about 0.07% Cholesteryl hemisuccinate tris salt (CHS), 0.33% n-dodecyl-beta-D-maltopyranoside (DDM), 0.33% Chaps, 0.33 mM DOPC/DOPS (7:3), and 1 protease inhibitor tablet per 50 ml buffer.

Cell membrane protein fractions can be obtained from any cell comprising the agent. Mammalian, insect, yeast, or bacterial cells can be used as sources of the membrane protein fraction. In certain embodiments, the cell can comprise a recombinant expression vector that provides for expression of an agent that is a membrane protein. In certain embodiments, the membrane protein can be an integral membrane protein or a peripheral membrane protein. Integral membrane proteins can include, but are not limited to, Type I integral membrane proteins, a Type II integral membrane proteins, a seven transmembrane domain (7-TM) integral membrane proteins, ion-channel proteins, and an ion-transporter proteins. In other embodiments, the membrane protein is a peripheral membrane protein. In certain embodiments where the membrane protein is a peripheral membrane protein, the peripheral membrane protein can be associated with the NABB by a lipid anchor. Seven transmembrane domain (7-TM) integral membrane proteins that can be used include, but are not limited, to G-Protein Coupled Receptors (GPCRs). Such GPCRs can be either those characterized by binding to a ligand or orphan GPCRs for which a binding ligand has yet to be identified. GPCRs that bind ligands including, but not limited to, amines, peptides, hormone proteins, rhodopsin, olfactory prostanoid, nucleotide-like compounds, cannabinoids, platelet activating factor, gonadotropin-releasing hormone, thyrotropin-releasing hormone and secretagogue, melatonin and lysosphingolipid and LPA. In other embodiments, the membrane protein can be a member of the cytochrome P450 family. Membrane proteins that can be used in the methods and compositions include, but are not limited to, chemokine receptors, cytokine receptors, receptor kinases, receptor phosphatases, receptors involved in cell-cell interactions, and cellular adhesion molecules. In certain embodiments, CCR5 receptors and variants thereof can be used. CCR5 receptor variants used include, but are not limited to, CCR5 variants deficient in glycosylation, tyrosine sulfation, or a combination thereof. In still other embodiments a combination of integral and peripheral membrane proteins can be expressed in the cell.

Cell membrane protein fractions can be obtained from any cell comprising the agent when the agent is a hydrophobic compound. The hydrophobic compound. can be provided to the cell by either endogenous production or exposure of the cell to exogenously supplied hydrophobic compound. Endogenous production can be mediated by either native processes, processes that occur in genetic variants, or processes are provided by recombinant DNA technology.

Purifying the NABB associated with at least one agent from the detergent depleted mixture can be accomplished by gel-filtration chromatography or other size exclusion methods. Examples of gel-filtration media include, but are not limited to, Sephacryl, Superdex, and Superose series. Affinity and/or immuno-affinity based purification methods can also be used either exclusively or in conjunction with size exclusion methods to effect purification of the NABB associated with just one membrane protein. Membrane proteins can in certain embodiments further comprise affinity purification tags that provide for purification. Such tags include, but are not limited to, peptide sequences that are recognized by immobilized antibodies or that recognize immobilized ligands. In certain embodiments, an affinity tag can be linked to the membrane protein via a cleavable or labile linkage that further facilitates purification. Such cleavable linkages include, but are not limited to, protease cleavage recognition sites. Alternatively, the apolipoprotein itself can comprise any of the aforementioned affinity purification tags that provide for purification. In certain embodiments, Zebrafish apolipoprotein A-I or a variants thereof comprising either N- or C-terminal affinity tags can be used. In certain embodiments, Zebrafish apolipoprotein A-I or a variants thereof comprising an N-terminal hexahistidine tag can be used.

Any phospholipid or phospholipid mixture that provides for bilayer formation and that is compatible with apolipoprotein A-I and the desired membrane protein can be combined with the membrane protein fraction and apolipoprotein A-I. In certain embodiments, such phospholipids can comprise a 6 to 20 carbon saturated or unsaturated fatty acid chain and a head group. Head groups include, but are not limited to, positively charged, negatively charged, zwitterionic, or uncharged head groups. Exemplary head groups include, but are not limited to, phosphatidyl choline, phosphatidyl ethanolamine, and phosphatidyl serine. Phospholipids that can be used include, but are not limited to, 1-Palmitoyl-2-Oleoyl-sn-Glycero-3-Phosphocholine (POPC), 1,2-Dimyristoyl-sn-Glycero-3-Phosphocholine (DMPC) or a derivative of either 1,2-Dioleoyl Phosphatidylethanolamine (DOPE) or 1,2-Dipalmitoyl-sn-Glycero-3-Phosphoethanolamine (DPPE), labelled derivatives thereof, or a combination thereof.

Any detergent that provides for inhibition of bilayer formation and that is compatible with apolipoprotein A-I and the desired membrane protein can be combined with the membrane protein fraction and apolipoprotein A-I. Detergents that can be used include, but are not limited to, sodium cholate, n-octyl-beta-D-glucopyranoside (OG), n-dodecyl-beta-D-maltopyranoside (DDM), 5-Cyclohexylpentyl beta-D-maltopyranoside (Cymal-5), 3-[(3-Cholamidopropyl)dimethylammonio]-1-propanesulfonate (CHAPS), or a combination thereof. In certain embodiments, methods provided herein permit use of detergents with CMC values of about 50 mM or less at a temperature of about 20 to 25 degrees centigrade.
Preparation and Use of NABB/Membrane Protein Compositions Comprising a Native Conformational Epitope for Eliciting an Immune Response Yet another aspect of this invention are methods for preparing and using NABBs associated with membrane proteins that contain a native conformational epitope. NABBs associated with a membrane protein that contains a native conformational epitope are useful for eliciting immune responses in various hosts. In particular, compositions comprising a purified NABB associated with at least one membrane protein containing a native conformational epitope, wherein the membrane protein does not contain the native conformational epitope when associated with a NABB by dialysis-mediated detergent depletion, methods of making such compositions, and methods of using such compositions are provided herein. Without seeking to be limited by theory, the rapid depletion of detergent(s) from a mixture comprising an apolipoprotein A-I, phospholipid(s), detergent(s), and a membrane protein provided by the instant methods of the invention can result in preservation of native conformational epitopes. In contrast, methods entailing the more lengthy dialysis mediated detergent removal steps entail protracted exposure of membrane proteins to detergents that may result in the loss of native conformational epitopes.

Presence of a native conformational epitope in a membrane protein can be determined by a variety of methods. One such method comprises exposing the NABBs associated with the membrane protein with an antibody that specifically recognizes the conformational epitope and determining the level of immunoreactivity. In certain embodiments, a membrane protein is regarded as not containing a conformational epitope when the immunoreactivity observed is less than about 30% of the immunoreactivity observed for a molar equivalent of the native protein comprising the conformational epitope, when using the same antibody that specifically recognizes the conformational epitope. In other embodiments, a membrane protein is regarded as not containing a conformational epitope when the immunoreactivity observed is less than about 20%, 10%, 5%, or 1% of the immunoreactivity observed for a molar equivalent of the native protein comprising the conformational epitope, when using the same antibody that specifically recognizes the conformational epitope.

Any of the methods disclosed herein for obtaining the NABB associated with at least one membrane protein that entail depletion of detergents within about one hour of mixture formation can be used to obtain immunogenic compositions provided herein. In certain embodiments, the cell based-methods comprising use of cell membrane protein fractions with apolipoprotein A-I can be used to obtain NABBs with associated membrane proteins for the composition. In other embodiments, the non-cell based methods comprising use of a mixture of one or more membrane proteins, apolipoprotein A-I, detergent(s), and phospholipid(s) can be used. Choice of the apolipoprotein A-I used may be based open the host that will be challenged with the composition. Thus, a human apolipoprotein A-I can be used to challenge human hosts, a bovine apolipoprotein A-I can be used to challenge bovine hosts, an equine apolipoprotein A-I can be used to challenge equine hosts, and so on. Nonetheless, an apolipoprotein A-I from a heterologous host can also be used to provide an immunogenic composition useful for challenging a host. Thus, heterologous apolipoprotein A-I proteins that can be used include, but are not limited to, a Zebrafish apolipoprotein A-I or variant thereof.

Although NABBs themselves are believed to function as adjuvants in eliciting immune responses, supplementary adjuvants can also be used in the compositions, methods of use, and methods of making provided herein. Such supplementary adjuvants include, but are not limited to, alum, detoxified lipid A, a muramyl peptide, a saponin, a T-helper (Th) peptide, or a combination thereof.

EXAMPLES

The following examples describe embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

Example 1

Description of Materials Used

Oligonucleotide primers were obtained from GeneLink (NJ), restriction endonucleases from New England Biolabs (Ipswich, Mass.). Lipids were obtained from Avanti Polar Lipids (Alabaster, Ala.). Detergents were obtained from Anatrace, Inc. (Maumee, Ohio). Fluorescent dyes were obtained from Invitrogen (Carlsbad, Calif.) and Atto-Tec (Siegen, Germany). Electron microscopy stains and grids were obtained from Electron Microscopy Sciences (Hatfield, Pa.). All other reagents were obtained as the highest grade available from Sigma-Aldrich, Inc. (St. Louis, Mo.). All UV-visible absorption spectroscopy experiments were performed in a Perkin-Elmer Lambda 800 UV-visible spectrophotometer. Buffer T: 25 mM Tris, pH 8, 125 mM NaCl, 1 mM $NaN_3$. Buffer H1: mM HEPES-MES-KOH, pH 6.9, 125 mM KCl, 2 mM $MnCl_2$, 2 mM $CaCl_2$, 1 mM EDTA. Buffer H2: 10 mM HEPES-MES-KOH, pH adjusted from 6.9 by using either 1N HCl (more acidic pH) or 1N KOH (more basic pH), 125 mM KCl. Buffer N1: 20 mM Tris pH 7, 0.1 M $(NH_2)SO_4$, 10% glycerol, 0.07% CHS, 0.018% DOPC, 0.008% DOPS, 0.33% DM. Buffer P2: 20 mM Tris pH 8, 0.6% (w/v) POPC, 0.4% POPS, 0.01% (w/v) NBD-DPPE, 1% (w/v) CHAPS. Buffer G1: 20 mM HEPES-MES-KOH pH 6.9, 0.3 M NaCl, 5 mM $MgCl_2$, 5 µM GDP.

Example 2

Amino Acid Alignment of Zebrafish Apolipoprotein A-1 and Human Apolipoprotein A-1

Amino acid sequences of *Danio rerio* apo A-I (NCBI accession number: NP_571203) and *Homo sapiens* apo A-I preproprotein (NCBI accession number: NP_000030) were downloaded from NCBI. The first 21 amino acids in the *D. rerio* apo A-I sequence and the first 24 amino acids in the *H. sapiens* apo A-I preproprotein sequence were discarded from the analysis (and subsequent constructs) as putative signal sequences. The resultant mature apolipoprotein A-I sequences from Zebrafish (SEQ ID NO: 1) and human (SEQ ID NO:2) were aligned using ClustalW.

Example 3

Cloning of Hexa-Histidine Tagged Constructs zap1, zap1Q26C and hΔap1

*D. rerio* apo A-I cDNA was generated by reverse transcriptase (RT-)PCR from 1 µg of *D. rerio* total RNA using the primers 5'-CAGGCTGATGCCCCGAC-3' (SEQ ID NO. 4) corresponding to N-terminus of the translated protein and 5'-TTATGCCTGGATGGCCTTGG-3' (SEQ ID NO. 5) corresponding to the C-terminus. Restriction sequences for NheI and HindIII were incorporated in the primer sequence upstream of the apolipoprotein cDNA sequence. RT-PCR was performed using a one-step RT-PCR kit (cMaster RT plus PCR™ system, Eppendorf). The cDNA obtained was cloned into the TOPO™ cloning vector (Invitrogen, Carlsbad, Calif.). The cDNA was subcloned using NheI and HindIII restriction endonucleases into pET28a(+) vector (Stratagene, La Jolla, Calif.), which was modified to contain a 6×His tag followed by a Precission™ protease (GE Healthcare, Piscataway, N.J.) cleavage site immediately upstream of the zap1 sequence, to give the vector pE28-ZAP1. To incorporate a site-specific maleimide label, a single Gln residue near the N-terminus was mutated to Cys (Q25C in SEQ ID NO:1) by site-directed mutagenesis of pE28-ZAP1 to give the vector pE28-Z1Q26C. The Zebrafish apolipoprotein A-1 used in the experiments described herein containing the glutamine to cysteine mutation is referred to herein as "zap1Q26C" (SEQ ID NO: 3). This glutamine to cysteine substitution corresponds to a substitution for glutamine at position 25 of SEQ ID NO:1. Human apo A-I cDNA was obtained from ATCC (MGC-12499) and cloned into a pET16a vector (Stratagene, La Jolla, Calif.) that was altered to have a N-terminal 6×His purification tag followed by a Factor Xa protease cleavage site to give the vector pE16-HAP1. All nucleotide sequences were confirmed by DNA sequencing (Genewiz, South Plainfield, N.J.).

Example 4

Expression and Purification of Hexa-Histidine Tagged apo A-1s

The corresponding vector was transformed into BL21 (DE3) Rosetta2 strain of *E. coli* (EMD Biosciences, Madison, Wis.) and plated on LB-agar containing appropriate antibiotics. BL21(DE3) Rosetta2™ strain of *E. coli*, which contains an additional plasmid coding for rare *E. coli* tRNAs (BL21DE3 Rosetta2) instead of codon optimizing the DNA, was chosen because zap1 cDNA contained some rare codons for *E. coli*. The bacterial strain is also deficient in proteases, since apo A-I being a flexible protein, may be susceptible to proteolysis in the bacterial cell. Evidence of truncated proteins was observed however, and may be attributed to aborted protein translation in *E. coli*. A single colony was grown in 250 mL LB media containing 50 □g/mL of antibiotics overnight at 37° C. with shaking as the starter culture. The starter culture was diluted 1:100 into 1.6 L of sterilized TB (Terrific Broth; GE Healthcare) media, incubated at 37° C. with shaking at 180 rpm and induced with 1 mM isopropyl-β-D-thiogalacto-pyranoside (IPTG) at $OD_{600}$ of 0.5-0.6. Cells were harvested by centrifugation after 3-4 hours. The cell pellet was resuspended in storage buffer (40 mM Tris pH 8, 0.3M NaCl, 2 mM PMSF, 5 mM 2-mercaptoethanol, 0.06 U/mL aprotinin and Complete EDTA-free protease inhibitor (one tablet per 50 mL; Roche Applied Science, Indianapolis, Ind.) and stored at 80° C. until further use.

The cell pellet was thawed and disrupted by a French press (Avestin, ON, Canada). Solid guanidine hydrochloride (Gn.HCl) was added to a final concentration 6M in the cell lysate and incubated at room temperature for 30 minutes followed by centrifugation at >25,000×g for 1 h. Alternatively, cells were lysed in detergent (1% Triton X-100). The apo-1 is mostly unfolded in 6M guanidine hydrochloride or 1% Triton X-100. The supernatant was filtered through a 0.45 □m filter and loaded onto a 5 mL Ni-Sepharose 6 FF column (GE Healthcare, Piscataway, N.J.) pre-equilibrated with buffer T (pH 8) containing 6M Gn.HCl and 25 mM imidazole. The column was washed sequentially with the following volumes and buffers: 2 column volumes (CV) of 6M Gn.HCl buffer T, 2 CV 2M Gn.HCl buffer T and finally 5 CV of Gn.HCl-free buffer T. The protein was eluted by an imidazole gradient on an Äkta Explorer 10 FPLC system (GE Healthcare). Gel-filtration chromatography was performed on a Superdex 200 26/60 column (GE Healthcare). The peaks were assayed for purity by SDS-PAGE. The pure, hexa-histidine tagged protein was called zap1.

Example 5

Labeling zap1Q26C with Alexa-488 Maleimide

A column-based approach was used to label the zap1Q26C mutant with Alexa-488 maleimide. A pre-packed 1 mL Ni-Sepharose 6 FF column was used for labeling the Cys mutant (zap1Q26C). The fluorophore was diluted from a 22 mM DMSO stock to make 2 mM of fluorophore in buffer T containing 2M Gn.HCl at pH 7.4. After binding zap1Q26C to the column and washing with buffer T+2M Gn.HCl at pH 7.4, the fluorophore was introduced with a syringe and the flowthrough was passed over the column again. The column was washed using a peristaltic pump with 4 CV of buffer T containing 2M Gn.HCl and finally 5 CV of Gn.HCl-free buffer T. The protein was eluted by introducing 2 CV of 300 mM imidazole+buffer T, pH 7.4, by a syringe. The collected fraction was pooled and subjected to gel-filtration on a Superdex 200 10/30 column. The peaks were assayed for purity and the labeling ratio was determined by comparing absorbance values at 488 nm (Alexa-488) and 280 nm (protein). A 0.9-1.0 (M:M) ratio of Alexa-488 to zap1Q26C was obtained under the above conditions.

Example 6

Purification of Rhodopsin and Rhodopsin Labeling

Rod outer segment (ROS) membranes were isolated from frozen dark-adapted bovine retinae (W.L. Lawson Co., NE). ROS membranes were solubilized in 1.5% (w/v) n-octyl-□-D-glucopyranoside (OG) containing buffer H1 and rhodopsin was purified by immobilized 1D4 antibody affinity purification according to Botelho, A. V. et al. *Biophys. J.* 91, 4464-4477 (2006). Fluorophore labeling of rhodopsin was done on ROS membranes with maleimide-functionalized Atto-655 fluorophore (Atto-Tec). Typically, 1 mg/mL rhodopsin in ROS was used for labeling in a 250 mL reaction volume. Atto-655 maleimide was diluted from a 22 mM DMSO stock to a final ratio of 9.0 fluorophore:rhodopsin (M:M). The mixture was shaken at 28° C. for 12.5 h under Ar and subsequently terminated by adding 10 mM DTT. The labeled ROS was washed thrice with 3 volumes of detergent free buffer H1 containing 1% fatty-acid free BSA. The ROS was then solubilized in 1.5% OG containing buffer H1 and rhodopsin purified by concanavalin A-sepharose affinity. The resin with bound rhodopsin was washed 5× with 1.5% OG containing buffer H1 and rhodopsin eluted in 1.5% OG containing buffer H1 with 100 mM α-methyl mannoside. The labeling stoichiometry was determined by comparing absorbance of the fluorophore and rhodopsin by UV-vis difference spectroscopy and was determined to be 0.8-1.0 (M:M) Atto-655:rhodopsin. Site-specificity of labeling was confirmed by digestion of labeled rhodopsin by V8 protease and detecting labeled fragments on SDS-PAGE. Rhodopsin labeling was done with Atto-655 in ROS to increase the selectivity for a single Cys on helix 8 (Cys316) to the fluorophore compared with the other Cys residues in the protein. Site-specificity of labeling was determined by digesting detergent-purified labeled rhodopsin with V8 protease.

Nanogold labeling of rhodopsin was performed on ROS membranes using monomaleimido-Nanogold following the manufacturer (Nanoprobes, Yaphank, N.Y.)-recommended conditions and concentrations. Briefly, monomaleimido-Nanogold was diluted from a 22 mM DMSO stock to a 9.0 (M:M) ratio of monomaleimido-Nanogold to rhodopsin in ROS (5 mg/mL) in buffer H1. The mixture was incubated under Ar at 28° C. for 16 h with shaking in a Thermomixer (Eppendorf, Westbury, N.Y.). The reaction was stopped by adding 5 mM DTT to the labeling mixture. The ROS membranes were washed thrice with 1% (w/v) fatty-acid free bovine serum albumin solution. The rhodopsin was purified in buffer H1 containing 1.5% OG and concanavalin A-Sepharose affinity. The beads were washed at least 5 times to remove non-specifically associated Nanogold, monitored by UV-visible spectrophotometry. The rhodopsin was eluted thrice using 100 mM α-methyl mannoside in 1.5% OG containing buffer. The labeling stoichiometry was determined by comparing the characteristic absorbance of Nanogold at 420 nm with rhodopsin absorbance at 500 nm determined by UV-vis difference spectroscopy and was found to be 0.8-0.9 (M:M) Nanogold:rhodopsin.

Example 7

Formation of Nanoscale Apolipoprotein Bound Bilayers (NABB)

A fluorescent lipid stock containing lissamine rhodamine B-sulfonyl DOPE (LRB-DOPE) doped POPC (1:100) was used for nanoscale apolipoprotein bound bilayers (NABB) formation according to the following method. A 1% (w/v) POPC solution was prepared by rapidly weighing POPC from a lyophilized stock and dissolving it in 1% (w/v) sodium cholate containing buffer H1. The POPC solution was subjected to several freeze-thaw cycles using liquid nitrogen followed by vortexing at room temperature to obtain a clear solution. A labeled lipid stock was prepared by drying a chloroform solution of lissamine rhodamine B-sulfonyl labeled DOPE (LRB-DOPE) in a pre-weighed glass round-bottom flask under a stream of Argon and put under high vacuum overnight to remove traces of solvent. The flask was weighed and the amount of dry labeled LRB-DOPE was calculated. The lipid was dissolved at 10 mg/mL in 1% (v/v) cholate containing buffer H1. The labeled lipid stock was obtained from 1:100 (v/v) mixture of LRB-DOPE and POPC solution, resulting in 1:100 Lissamine rhodamine B labeled lipids.

The NABB formation with or without rhodopsin incorporated is a self-assembly process between NABB components triggered on detergent removal. A molar ratio of 150 POPC:2 zap1 in 1.5% (w/w) sodium cholate and 1.5% (w/w) OG containing buffer T was formed NABBs without incorporation of the membrane protein. For each rhodopsin molecule to be incorporated, 34 POPC molecules were subtracted from the initial reaction mixture.

Example 8

Detergent Removal Methods

Detergent removal was accomplished either dialysis-mediated removal (Method A) or column extraction (Method B). Method A was performed by dialyzing the samples using Slide-A-Lyzers (Pierce Biotechnology, Rockford, Ill.) containing 10 kD MW cutoff membrane and 0.5-3 mL volume against 1000 volumes of detergent free buffer for 36 h at 4° C. with 2-3 buffer exchanges.

Method B (column extraction) was performed by loading the reaction mixtures onto pre-equilibrated Extracti-Gel D (Pierce Biotechnology) columns typically of 1 mL resin volume and approximately 4 cm column height made by loading Extracti-Gel D slurry into empty Sep-Pak columns (Waters Corp., Milford, Mass.). For Extracti-Gel D reconstitutions, about □mL of the detergent-containing initial reaction mixture was layered on top of the packed 1 mL resin. The solution was allowed to enter the column completely by gravity flow and then eluted by adding 3 to 4 aliquots of 0.2 mL of detergent free buffer and collecting the eluate in equal volumes. The NABBs elute over 2-3 fractions, as determined by UV-vis spectroscopy. The time to complete the elutions was approximately 30 minutes. The rhodopsin-NABBs (rho-NABBs) used for assays were formed by Method B unless otherwise stated. Once formed, the rho-NABBs were purified by gel-filtration chromatography on a Superose 6 10/30 column (GE Healthcare, Piscataway, N.J.) and used within 1-2 days for the assays.

Example 9

Immunoaffinity Purification of Rhodopsin-NABBs

Rho-NABBs prepared with a ratio of <2 rho/NABB were enriched by affinity purification of rho-NABBs on 1D4-sepharose beads. The detergent-free reconstitution product containing rhodopsin, zap1 and POPC was incubated with 250-400 □L of 1D4-linked Sepharose beads in buffer H1 for 3-4 h at 4° C. on a nutator. The beads were washed 5× and the bound products were eluted using the 1D4 nonapeptide epitope TETSQVAPA.

Example 10

Affinity Purification of NABBs

NABBs with or without rhodopsin were enriched by affinity purification on Ni-NTA beads. The detergent-free reconstitution product of zap1 (with or without fluorescent label), POPC and rhodopsin was incubated with 50-□□L Ni-NTA beads (Qiagen Inc., Valencia, Calif.) in buffer H2, pH 8, for 1 h at 4° C. on a nutator. The beads were washed 5× and the bound products were eluted using 10 mM EDTA.

Example 11

Decoration of Rhodopsin in NABBs by Fab Fragments

Fab fragments from 1D4 were generated by proteolytic cleavage of 1D4 by papain, followed by gel-filtration chromatography. Fab fragments were incubated at equimolar ratio to the rhodopsin in NABBs with gentle nutation in the presence of concanavalin A-Sepharose beads overnight at 4° C. The beads were washed thrice with 5 volumes of buffer. The Fab-rho-NABB complex was eluted with 100 mM □-methyl mannoside containing elution buffer. The elutions were concentrated using an Amicon-15 centrifugation filtration device (Millipore, Billerica, Mass.) with a 50 kD MW cut-off and the buffer was exchanged simultaneously with □-methyl mannoside free buffer. The complex was then subjected to gel-filtration chromatography on a Superose 6 10/30 column. The peak fraction was used for analysis by electron microscopy.

Example 12

Negative-Stain Transmission Electron Microscopy

A freshly prepared NABB sample (5 □L) at a protein concentration of approximately 5-10 □g/mL was applied to a 400 mesh carbon coated copper grid that was glow discharged for 10-20 s prior to sample application. The NABB sample was blotted after 1 minute and an equal volume of 1% uranyl acetate (UA) was immediately applied. The stain was gently wicked away and the staining was repeated. Grids were imaged under 80 keV using a Jeol 1230 transmission electron microscope equipped with a 1 k×1 k CCD camera. Images were acquired at about 1-2 μm underfocus for obtaining contrast. Nanogold images were acquired using 0.5% UA stain and at lower defocus (200-500 nm) to achieve highest density and contrast of the gold clusters.

Example 13

Thermal Stability Assay of Rhodopsin in NABBs and in ROS

Rho-NABBs were formed by dialysis (Method A) against buffer H1, pH 7, followed by Ni affinity purification in the dark. Aliquots of 1 μM rhodopsin in NABBs or ROS or detergent containing buffer H1 were incubated in 0.5 mL Eppendorf tubes at various temperatures in a thermomixer without shaking. After 15 minutes of incubation, each aliquot was kept on ice until it was used for a UV-visible scan in a Perkin-Elmer Lambda 800 UV-visible spectrophotometer at room temperature. The sample was then bleached under yellow light (>495 nm wavelength) for 30 s in the presence of 50 mM hydroxylamine. The intact rhodopsin content of the sample was estimated by calculating the difference in absorption intensity between the dark and light spectra at 500 nm.

Example 14

Meta-II Decay Assay

Decay of rhodopsin Meta-II state in NABBs was followed by tryptophan fluorescence. Rhodopsin concentration was adjusted to 10 nM in 10 mM HEPES-MES-KOH buffer pH 6, 125 mM KCl, 2 mM $MgCl_2$ in a magnetically stirred cuvette. The temperature was maintained at 20° C. by a circulating water bath. Tryptophan fluorescence was recorded in a SPEX Fluorolog tau-3 spectrofluorimeter, equipped with a 450 W Xenon arc-lamp and excitation wavelength of 295 nm with 0.2 nm bandpass. A UV-bandpass filter (Hoya U-340, Edmund Optics, Barrington, N.J.) was used in addition to the emission monochromator, set to 330 nm and 10 nm bandpass. The signal was integrated for 2 s. Data was recorded for 30 minutes in 30 s intervals. The rhodopsin sample in the cuvette was bleached for 15 s using a fiber-optics 150 W illuminator at full intensity with a yellow filter (model A-200, Dolan-Jenner Industries, Boxborough, Mass.) after obtaining a dark baseline for 3 minutes.

Example 15

Regeneration of Opsin in NABBs

Opsin-NABBs were generated by photobleaching μμ of 1rho-NABB in buffer H2, pH 6, for one minute and incubating the photobleached sample at room temperature for more than 2 h. 11-cis-retinal was diluted from a 1 mM ethanolic stock to a final concentration of up to 100 μM in approximately 1 μM empty NABBs and vortexed vigorously to ensure proper mixing. Concentration of 11-cis-retinal was determined by absorption at 378 nm using $\epsilon_{378}$=24,940 $M^{-1}$ $cm^{-1}$. Under dim light, 11-cis-retinal-loaded NABBs were gently added by a microcapillary pipette tip to a final concentration of 0.5 μM 11-cis-retinal to a stirred microcuvette containing 700 μL of 0.5 μM opsin-NABBs. Absorbance was monitored at 520 nm, with a slit width of 0.5 nm, integration time of 1 s and time interval of 3 s. After saturation of the absorbance signal, 50 mM of $NH_2OH$ was gently added from a 3.5M $NH_2OH$ stock. Finally, the sample was bleached using yellow light (>495 nm filter).

Example 16

Transducin Activation Assay

A 1rho-NABB sample for transducin activation was isolated by immunoaffinity purification of a one rho per 100-NABB sample. 2rho-NABB was prepared from a two rho per NABB sample. Both samples were prepared using non-labeled POPC and purified by gel-filtration chromatography in the dark. Activation of holotransducin (Gt) by rhodopsin incorporated in NABBs was analyzed by the tryptophan fluorescence assay of the $Gt_\alpha$, subunit by adding 10 nM of rhodopsin-NABBs to 100 nM Gt in 10 mM Tris buffer, pH 7.4, 100 mM NaCl, 2 mM $MgCl_2$, 5 μM GDP in a continuously stirred cuvette thermostatted at 10° C. in a SPEX Fluorolog-II spectrofluorimeter. The sample was excited at 300 nm with 2 nm slit width, and emission was recorded at 340 nm with a 12 nm slit width. GTP-γS was added to a final concentration of 5 μM in the cuvette. The cuvette was then illuminated by 543 nm light from a HeNe laser and the fluorescence intensity was recorded under constant illumination. The curve obtained was analyzed by fitting an exponential corresponding to pseudo-first order kinetics.

Example 17

Isolation of Heterologously Expressed CCR5 Receptor and Incorporation in NABBs

HEK-293 cells stably expressing Chemokine Receptor 5 (CCR5) were harvested and the cell pellet stored in PBS buffer containing protease inhibitors at −80° C. Cell pellets corresponding to 2×10 cm plates were thawed on ice and lysed using 500 mL of buffer N1. The solution was sonicated using a probe-tip sonicator for 6×1 s pulses with 10 s cooling on ice. The tube was then incubated at 4° C. with gentle mixing for 30 minutes. The tube was centrifuged at 20,000×g for 20 minutes at 4° C. The supernatant was collected and mixed with 50 mL of a 1D4-sepharose slurry loaded with 2 mg/mL of 1D4 and incubated at 4° C. with gentle mixing for 30 minutes. The mixture was centrifuged and washed with 500 mL of buffer P2. The 1D4-bound protein was eluted by adding 50 mL of buffer P2 containing 1D5-nonapeptide. Zap1 was added to the eluate at a final concentration of 80 μM. The mixture was vortexed, incubated on ice for 30 minutes and applied to a pre-equilibrated 500 mL Extracti Gel-D column at 4° C. Elution was carried out under gravity flow by addition of detergent free buffer to the column and collecting 50 mL fractions. The fractions were monitored for protein elution by absorbance at 280 nm. The protein containing fractions were pooled and applied to a Superose 6 PC 3.2/30 gel-filtration column. The eluted peaks corresponding to the NABB elution were applied to 50 μL of 1D4-sepharose. The resin was washed with buffer P2 and eluted with 1D5 containing buffer P2. Aliquots from different stages of this protocol were used to assay for CCR5 using ELISA or Western blot analysis.

Example 18

Sandwich ELISA to Detect GPCR in NABBs

The primary (capture) antibody was diluted to 1 μg/mL in 1×PBS pH 7.2 and 100 μL was added to each well of the microplate (Costar clear-bottom, black 96-well). The plate was stored overnight at 4° C. The plate wells were washed twice with PBS containing 0.05% Tween-20 and once with PBS and 200 µL of 10 mg/mL (1%) fatty-acid free BSA in PBS. The plate was either incubated at room temperature for 2 hours or overnight at 4° C. G-protein coupled receptor (GPCR)—NABBs were added to the respective wells in a final volume of 100 µL. GPCR-NABB was diluted in PBS containing 1 mg/mL (0.1%) BSA. The microplate was incubated at 4° C. overnight to ensure complete binding of epitope on the GPCR-NABB to the capture antibody. The analyte was then washed 3 times with 0.1% BSA-PBS using 200 µL per wash. HRP-conjugated secondary (detection) antibody was added at 0.5-1.0 µg/mL to each well (depending on the antibody affinity to the second epitope on the GPCR-NABB). The plate was incubated at room temperature for 2 hours. The wells were washed 3-4 times with 0.1% BSA-PBS. A fresh working solution of Amplex Red and $H_2O_2$ was prepared from DMSO stock of Amplex Red and 3% $H_2O_2$ according to the manufacturer recommended protocol (Invitrogen, CA). 50 µL of the Amplex Red working solution was dispensed in each well and the plate was incubated for 30 minutes at room temperature, protected from light. The fluorescence in the wells was measured using a Cytofluor-II spectrofluorimeter with excitation at 530 nm and emission at 590 nm.

Example 19

High-Throughput G-Protein Activation Assay

A black, C-bottom 96-well plate was used for the high-throughput G-protein activation assay. 25 µL of purified G protein or its subunits were added to the microplate wells from a 150 mM protein stock. The added proteins were either $G_{i1}\alpha$ subunit, $G_{i1}\alpha$ with transducin βγ subunits, or holotransducin (Gt), with 25 µl of buffer G1 without GDP. CCR5-NABBs were incubated with 50 nM RANTES on ice for 30 minutes. 100 µL of CCR5-NABB solution with and without RANTES were added to the respective wells and the microplate incubated at room temperature for 15 minutes. 60 µL of BODIPY-FL-GTPγS was added from a 1 µM stock to all wells using a multi-channel pipettor. The plate was shaken for 30 seconds, covered and incubated at room temperature for 5 minutes. The fluorescence in the wells was recorded using a Cytofluor II microplate reader with excitation wavelength at 485 nm and 20 nm bandpass, emission wavelength at 530 nm and 25 nm bandpass. The gain was set to 95 and 15 reads were integrated for each well. The fluorescence values from the wells containing BODIPY-FL-GTPγS and no G protein was subtracted from the rest of the data as background. The fluorescence values from wells containing the CCR5-NABBs with no RANTES was subtracted from RANTES-containing wells to determine the RANTES-specific response.

Example 20

Comparative Analysis of Zebrafish apo A-1 and Human apo A-1

To identify amino acid patterns between Zebrafish and Human apolipoproteins, an amino acid sequence alignment was performed (FIG. 1a). Invariant proline residues occur every 22 or 11 amino acids in zebrafish apo A-1. Thus, the length of zebrafish apo A-I may be divided into tandem 22/11-mer helices that interact with the lipid side chains and are punctuated by proline 'hinges', similar to the lipid-binding mechanism hypothesized for human apo A-I. The alignment also showed a general conservation of the chemical type of the amino acid residue in zebrafish apo A-I at the corresponding positions of the human apo A-I. The sequence similarity implies a similar lipid binding mechanism and amphipathicity of zebrafish apo A-I compared with human apo A-I. Hydropathy analysis (FIG. 1b) showed the C-terminal residues may not be as important for lipid binding in zebrafish apo A-I compared with human apo A-I. N-terminal tails of both zebrafish and human apo A-I showed a conserved pattern of high hydrophobicity, indicating a possible role of the N-terminal residues of zebrafish apo A-I in lipid binding. It was discovered that Zebrafish apo A-1 contains a proline at position 186, which is the region between putative helices 7 and 8, where human apo A-1 lacks a proline at the same position. The presence of Pro186 in zebrafish apo A-1 may provide an explanation for the monodisperse nature of discoidal lipoprotein particles formed by zebrafish apo A-1-NABBs when compared to human apo A-1.

Example 21

Effect of POPC:zap1 Ratios on NABB Formation

It was discovered that different POPC:zap1 ratios result in the formation of three distinct NABB populations in addition to vesicles. As shown in FIG. 2, a POPC:zap1 ratio of 25:1 resulted in NABB with maximal Stokes diameter of about 10 nm. A POPC:zap1 ratio of 75:1 resulted in NABB with maximal Stokes diameter of about 11.6 nm. A POPC:zap1 ratio of 100:1 resulted in NABB with maximal Stokes diameter of about 17 nm. Investigations using human apo A-1 with POPC report diameters of 8.5 nm, 12.0 nm, and 15.5 nm, whereas human Δ1-43 apo A-1 forms diameters of 8.5 nm, 12.5 nm, and 16.5 nm (see, Rogers et al., *Biochem.* 36, 288-300 (1997)). Moreover, zap1-POPC NABB tend to form a homogeneous disc population, while human Δ1-43 apo A-1 forms discs with a broad and heterogeneous size distribution. Negative-stain transmission electron microscopy of NABB produced at a POPC:zap1 ratio of 75:1 showed well-defined separated NABBs with average diameters of 10-13 nm and thicknesses of about 5 nm.

Example 22

Characterization of zap1 NABB Formation Methods

It was discovered that NABBs formed using a detergent-removing gel (e.g., Extracti-Gel D, Method B) formed sharper gel-filtration profiles compared to detergent dialysis (Method A). The detergent-removing gel removed detergents with comparatively low critical micellar concentration values and accelerated the rate of NABB formation. The detergent dialysis method, however, is only efficient for removing detergents with relatively high critical micellar concentration values.

NABB formation is a self-assembly process triggered by detergent removal upon mixing and incubating the NABB components. Further, NABB formation does not require the inclusion of a membrane protein. For example, a molar ratio of 150:2 POPC:zap1 in 1.5% (w/w) sodium cholate and 1.5% OG containing buffer T formed NABB in the absence of membrane protein.

Example 23

Membrane Protein Incorporation in NABBs

It was discovered that membrane proteins can become incorporated into the NABB. The dim-light visual receptor rhodopsin (rho), considered a model system for GPCRs in terms of GPCR structure and the downstream G protein signaling mechanism, was used to investigate the incorporation of membrane proteins into NABB. Rho-NABB complexes were made with Alexa-488-conjugated zap1Q26C, N-(lissamine rhodamine B sulfonyl)-1,2-dioleoyl-sn-glycero-3-phosphoethanolamine (LRB-DOPE)-doped POPC, and Atto9-655-labeled rho where the starting reconstitution stoichiometry was one rho per 10 NABBs and subjected to gel filtration. See, FIG. 3a. Different starting molar ratios of rhodopsin to zap1 and POPC (NABB components) were used to form NABBs and subjected to small-scale batch purification using Ni affinity. See, FIG. 3b. The unbound fraction contains rhodopsin in vesicles and/or aggregates. UV-visible spectra of rho-NABBs made with different rhodopsin concentrations at a constant zap1 concentration after Ni affinity purification is shown in FIG. 3c. The final $A_{500}:A_{280}$ ratios were in good agreement with the initial stoichiometries of the reactions. Thus, rhodopsin incorporation into NABBs is efficient and controllable.

Example 24

Membrane Protein Stoichiometry and Orientation in NABBs

It has been discovered that NABBs may be used to isolate either one or two membrane proteins. Rho-specific labels with no crossreactivity with the lipid or apolipoprotein in the NABB were used to visualize rho incorporated in NABBs. Rho was labeled with Nanogold and imaged by negative stain electron microscopy at very dilute rho-NABB concentrations. As shown in FIG. 4a, more than 80% of the selected particles had at least two rhos and approximately 70% of particles contained exactly two rhos. 2rho-NABBs and 1rho-NABBS are shown in FIG. 4b. Thus, NABB may be used to isolate either one or two receptors—a phenomenon that is not possible to achieve in detergent micelles.

It has also been discovered that NABBs are an effective tool to image complexes of transmembrane receptors with associated signaling molecules. Rho-NABBs were imaged as a macromolecular assembly with anti-rho Fab fragments bound to the C-terminus of rho in NABBs to determine the orientation of multiple incorporated rhos. The formation of a stable 2Fab-rho-NABB complex was confirmed by fast protein liquid chromatography. See, FIG. 4c, top panel. FIG. 4c, bottom panel shows an electron micrograph of the macromolecular complex.

Fab-labeled rho-NABBs were analyzed to determine the relative orientation of two rhos in a single NABB. The set of selected particles were subjected to visual inspection and classified into either anti-parallel or parallel from the relative orientation of nanogold or Fab density with respect to the central lipoprotein density. Single particles picked from high defocus (≈−3 um) images of 2Fab-rho-NABB particles to classify the orientation of the C-termini of the two incorporated rhodopsins with respect to each other were analyzed. Particles where the zap1 belt was oriented perpendicular to the plane of the grid were analyzed as these particles were the ones where the Fab positions could be detected unambiguously with respect to the belt. See, FIG. 4c, bottom panel. Analysis of single particle images of Fab labeled 2rho-NABBs shows that approximately half of the NABBs containing two rhos contained rhos positioned in an antiparallel orientation with respect to each other. See, FIG. 4d. The orientation if Fab particles is depicted in a cartoon representation below each electron micrograph. Thus, NABBs are an effective tool to image complexes of transmembrane receptors with associated signaling molecules.

Example 25

Enhanced Thermal Stability of Membrane Proteins in NABBs

It was discovered that GPCRs showed enhanced thermal stability upon incorporation into NABBs. Thermal denaturation of rhodopsin in NABBs was compared with rhodopsin in rod outer segment (ROS) membranes and detergents commonly used for rhodopsin biochemistry. Thermal denaturation of rhodopsin occurs at a higher threshold temperature when it is in rod disc membranes compared with detergent (Hubbard *J. Gen. Physiol.* 42, 259-280 (1958); Knudsen and Hubbell *Membr. Biochem.* 1, 297-322 (1978)). We observed that the denaturation temperature of rhodopsin in NABBs is similar to rhodopsin in ROS. See, FIG. 5a. The data indicates that increasing the hydrophobic chain lengths of detergents (OG to DM), and substituting the non-ionic head group (OG or DM) by the zwitterionic head group of phospholipids (in NABBs or ROS membranes) both lead to substantial increase in thermal stability. There seems to be a slight decrease in the denaturation temperature when two rhodopsins inhabit a NABB compared to a single rhodopsin per NABB which may reflect the difference in the number of POPC molecules surrounding the rhodopsins and/or packing defects of the lipids in the reduced space between rho and apo A-I. The stoichiometry at the start of the self-assembly of the two rho per NABB particle has only 42 lipids surrounding each rhodopsin (21 per leaf of the bilayer). While this number of lipids may be comparable to the number of lipids surrounding rhodopsin in ROS (Miljanich and Dratz 1982), it is only 35% of the 116 lipids surrounding rhodopsin in a one rho/NABB case. The remarkable thermal stability of rhodopsin(s) in a NABB indicate that a minimal amount of lipids surrounding rhodopsin is sufficient to preserve its conformational state and thermal stability may not depend upon long range lipid interactions.

Enhanced thermal stability upon incorporation into NABBs is particularly striking since many GPCRs show time-dependent loss of activity in detergents. (See, Navratilova et al. *Anal. Biochem.* 339, 271-281 (2005)). Thus, long-term exposure to detergents may be avoided using the rapid detergent-removing gel method for NABB formation. Moreover, thermal stability of membrane proteins such as rho may likely be enhanced by shielding the transmembrane hydrophobic area from water and satisfying specific chemical interactions with phospholipids on the protein surface.

Example 26

Meta-II Decay and Regeneration of Opsin in NABBs

Metarhodopsin II (Meta-II) decay of rhodopsin was followed by monitoring the change in Trp fluorescence to determine the Meta-II decay kinetics of rhodopsin(s) incorporated in a NABB. It was discovered that the Meta-II intermediate in one rho-NABBs has a half-life of 17 minutes and Meta-II in two rho-NABBs has a slightly longer half-life of 20 minutes. See, FIG. 5b. These values correlated with our data showing differences in the fraction of deprotonated Schiff base formed upon actinic light exposure and are in good agreement with previous reports of rhodopsin Meta-II decay assays (Heck et al., *J. Biol. Chem.* 278, 3162-3169 (2003); Jastrzebska et al. *J. Biol. Chem.* 279, 54663-54675 (2004)).

It was further discovered that opsin-NABB formed after Meta-II decay of rhodopsin regenerated rapidly and quantitatively in the presence of stoichiometric amounts of 11-cis-retinal. See, FIG. 5c. 11-cis-retinal serves as an inverse agonist and keeps the receptor in an inactive conformation in the dark. Absorbance at 520 nm was not affected by the absorption peak of free retinal (378 nm) or nonspecific Schiff base formation. The rapid regeneration of opsin in NABBs compared with opsin in DM is likely a result of the dramatic difference in the partial volume fraction of the lipidic environment. A recovery of the characteristic difference spectra and lack of hydroxylamine sensitivity under conditions minimizing photobleaching implies that the added 11-cis-retinal forms a specific, protonated Schiff base linkage at Lys-296 of opsin to form regenerated rhodopsin. Photobleaching the sample in the presence of hydroxylamine greatly accelerates the decay of Meta-II. In the presence of the deprotonated Schiff base form of retinal, hydroxylamine leads to the formation of a stable retinal oxime, a phenomenon that efficiently sequesters the chromophore out of the opsin.

Example 27

Transducin Activation by One and Two Rhos in NABB

Rates of transducin activation by rho-NABBs containing predominantly either one or two rhodopsins per particle were measured. See, FIG. 5d. The data were fit to an exponential of the form:

$$y = a^-_1 a_2 e^{-kx}$$

with a rate constant k. 1rho-NABB gave an apparent pseudo first-order rate constant ($k_{obs}^{(1)}$) of $6 \times 10^{-3}$ s$^{-1}$ and the 2rho-NABB sample gave a value ($k_{obs}^{(1)}$) of $3 \times 10^{-3}$ s$^{-1}$. Since both samples contain the same rhodopsin concentration, the number of catalytic centers for transducin activation is the same in the monomers and dimers. If the dimers are a mixture of N different equally probable species and only one of them is active, then the activity of this species is N-times the activity of the monomer. The maximum activity of the parallel (physiologically relevant) rho dimer may thus be calculated by assuming that only the parallel dimer is responsible for the observed transducin activity. As suggested by electron microscopy imaging, N equals two, and considering only the parallel dimer to be active, the catalytic center activity (Segel (1993) Enzyme Kinetics, 1, 79-80 Wiley-Interscience, New York, N.Y.) of the dimer is same as that of the monomer. Consequently, the dimer is equally efficient in activating transducin compared with the monomer.

The statements above may be rationalized further by comparison of transducin activation by rhodopsin in monomer and dimer form assuming it to be an enzyme-catalyzed reaction between rho (enzyme) and transducin (substrate).

Example 28

Incorporation of CCR5 Receptor in NABBs and Sandwich ELISA with Conformation Sensitive Antibody It has been discovered that chemokine receptor 5 (CCR5) can be incorporated into NABB at high yield and efficiency. CCR5 was incorporated into NABBs starting from HEK-293 cell pellets expressing CCR5. Cells were lysed in a mixture of lipids and detergents reported to preserve CCR5 stability (Navratilova et al. *Anal. Biochem.* 339, 271-281 (2005); Navratilova et al. *Anal. Biochem.* 355, 132-139 (2006)). The CCR5 fraction was enriched using 1D4-sepharose beads and the buffer was exchanged to buffer H1 containing POPC/POPS and CHAPS. The CCR5 was eluted with 1D5 nonapeptide, and purified zap1 was added. NABB formation was performed by detergent removal using an Extracti Gel-D resin, yielding NABBs, as determined by a single peak in the gel-filtration step. See, FIG. 6. Eluted fractions were analyzed by sandwich ELISA using 2D7 capture and 1D4 probing antibodies. 2D7 recognizes a split epitope on the extracellular side of CCR5 only when the epitope are spatially close, and is therefore considered to bind to the correct conformation of CCR5 (Khurana et al. *J. Virol.* 79, 6791-6800 (2005)). Heat denaturation abolishes 2D7 binding to CCR5. The basal response was calculated using NABBs without incorporated membrane protein, prepared under identical conditions and assayed on the same ELISA plate at similar protein concentration. Since 2D7 is a conformation sensitive antibody, the ELISA data indicates that rapid incorporation of CCR5 into NABBs preserves the native conformational state of the receptor.

Example 29

Detection of Correctly Folded CCR5 in NABBs

Conformational stability of the extracellular side of CCR5 after exposure to different detergents was determined by a sandwich ELISA using 2D7 and 1D4 antibodies. See, FIG. 7. 1D4 monoclonal antibody recognizes an engineered linear amino-acid sequence at the C-terminal tail of CCR5. The amount of CCR5 bound to the 2D7 capture antibody was measured by detecting the binding of the second antibody-HRP-linked 1D4, and adding a fluorogenic HRP substrate in the microplate wells. HEK-293 (clone 18) cell aliquots were lysed using buffer (20 mM Tris pH 7, 150 mM NaCl, 1 mM EDTA) supplemented with detergents (1% w/v) and lipids (1% w/v total lipid) at 4° C. for 1 h. The samples were incubated at room temperature for 30 minutes before loading on the 96-well plate. Sample 2 was kept in a 95° C. water bath immediately after lysis for 5 minutes, followed by 30 minutes room temperature incubation. Sample 7 was processed from a cell aliquot lysed under conditions of Sample 1, followed by detergent removal.

To measure total amount of CCR5 in NABBs, 1D4 antibody was used as the capture antibody and HRP-linked hexahistidine binding antibody (6H) was used as the detection antibody to recognize the hexa-histidine tag on zap1. HEK cells solubilized in buffer containing dodecyl maltoside (DDM), CHAPS and a 1:1 (w/w) mixture of DOPC and POPC lipids gave the highest ELISA signal (sample 1). Heat treatment of this sample, followed by thawing at room temperature destroyed binding to 2D7 antibody (sample 2). Sample 2 served as a negative control for this ELISA, since it shows that the final ELISA signal is due to specific initial binding to 2D7, and not because of non-specific binding to the microplate well. Heat denaturation of CCR5 destroyed the native conformation of the extracellular loops (including ECL 2) resulting in loss of binding to 2D7.

Solubilization conditions using different detergents were investigated (samples 3-6) at 1% (w/v) concentrations. All the detergents were above their CMC values at these concentrations. The samples were incubated for 30 minutes at room temperature. DDM was discovered to be the best detergent for stabilizing the 2D7 epitope, with a signal that was 65% of sample 1. Reconstitution of a sample solubilized in conditions identical to sample 1 into NABBs using POPC and zap1 gave a signal that was 92% the signal of sample 1. Thus, it was discovered that rapid incorporation of CCR5 into NABBs preserves the native conformational state of the receptor as determined by the ELISA data. There is likely to be a difference in the extent of antibody binding by receptors in detergent micelles and in NABBs because of lesser accessibility of the epitope to the antibody and the charged phospholipids headgroups in NABBs. Considering this binding difference, the signal of sample 1 and sample 7 may be virtually identical. Incorporation of membrane proteins in NABB, however, preserves the native conformational state of the membrane proteins. Therefore, incorporation of membrane proteins in NABB provides a novel method for presenting membrane proteins in their native conformational state to antibodies rather than in their denatured state.

Example 30

Ligand Mediated Activation of CCR5 in NABBs

CCR5 activation of G protein was measured by binding of a fluorescently labeled nucleotide analog BODIPY-FL-GTPγS. BODIPY-FL-GTPγS binds to activated G protein and undergoes an increase in fluorescence quantum yield upon binding to the G-protein α-subunit (McEwen et al. *Anal. Biochem.* 291, 109-117 (2001)). The fluorescence increase of BODIPY-FL-GTPγS was measured using CCR5-NABBs with or without ligand. Rhodopsin-NABBs and holotransducin were used as a positive control. $Gi_1$ α-subunit ($Gi_1$α) was heterologously expressed and purified from *E. coli*. The $Gi_1$ α subunit did not contain post-translational modifications (prenylation or myristoylation) that are present in native Gα subunits. Holotransducin (Gt) was isolated from bovine retinae and transducin beta-gamma subunits (Gtβγ) were derived from holotransducin. Fluorescence intensity was calculated relative to that of a mixture of G protein and empty NABBs.

It was discovered that CCR5-NABB efficiently activated G-protein in the presence of the heterotrimeric Gi protein as well as holotransducin. Stimulation of CCR5 in NABBs by 50 mM RANTES produced up to 30% enhancement of B-GTPγS binding to the G protein, compared with unstimulated CCR5-NABBs (FIG. 8). The largest increase in BODIPY-FL-GTPγS was observed when βγ subunits from transducin were mixed in equimolar ratio with $G_{i1}$α. The results indicate the requirement of a heterotrimeric G protein to observe the activity of CCR5. The α-subunit of the G protein is mostly in contact with the cytoplasmic side of the GPCR. However, CCR5 does not seem to couple efficiently with $G_i$α alone. βγ subunits may be required for efficient activation of the G protein α-subunit. In this assay, βγ subunits may increase the accessibility of the $G_{i1}$ α subunit to the NABB due to the presence of a lipid anchor on the γ-subunit. It is also possible that βγ-subunits modulate an increase in the receptor mediated GTP uptake by the α-subunit by affecting the conformational change in the G protein.

B-GTPγS uptake in the presence of unstimulated CCR5-NABBs was detected (FIG. 8A). Stimulation of CCR5 in NABBs by 50 mM RANTES produced up to 30% enhancement of B-GTPγS binding to the G protein, compared with unstimulated CCR5-NABBs (FIG. 8B). A certain basal level of constitutive GPCR activity is common for GPCRs in the absence of an inverse agonist (Bartfai, Benovic et al. 2004). Under the assay conditions, a 10-15% greater binding of B-GTPγS was observed in the presence of CCR5-NABBs without ligand compared with empty NABBs alone. Samples with RANTES showed a significantly higher increase in signal.

These results demonstrate BODIPY-FL-GTPγS binding assay is a convenient and rapid method to assay for effector mediated G protein activation using purified CCR5-NABBs with purified G proteins. In vitro assays of small-molecules affecting ligand binding to CCR5 in the absence of G proteins may not be accurate in predicting the in vivo effects. A series of cell-based and membrane-based assays have determined that CCR5 couples to both Gi as well as Gq class of G proteins (Mueller, Mahmoud et al. 2006; Springael, de Poorter et al. 2007). However, there have been no reports of assays of CCR5 with purified G proteins. Thus, using CCR5-NABBs with purified G proteins in the BODIPY-FL-GTPγS binding assay is a convenient and rapid method to assay for effector mediated G protein activation.

The discussion of the references herein is intended merely to summarize the assertions made by their authors and no admission is made that any reference constitutes prior art. Applicant reserves the right to challenge the accuracy and pertinence of the cited references.

In view of the above, it will be seen that the several advantages of the invention are achieved and other advantageous results attained. As various changes could be made in the above methods and compositions without departing from the scope of the invention, it is intended that all matter contained in the above description and shown in the accompanying drawings shall be interpreted as illustrative and not limiting in a limiting sense. Thus, the breadth and scope of the present invention should not be limited by any of the above-described exemplary embodiments, but should be defined only in accordance with the following claims appended hereto and their equivalents.

What is claimed is:

1. A method for obtaining a substantially homogeneous population of nanoscale apolipoprotein bound phospholipid bilayers (NABBs) associated with at least one recombinant membrane protein, said method comprising:

a) obtaining a cell membrane protein fraction comprising one or more recombinant membrane proteins;

b) combining a Zebrafish apolipoprotein A-I with said cell membrane protein fraction to obtain a mixture, wherein said mixture is substantially deficient in NABB and comprises one or more phospholipid(s) and one or more detergent(s);

c) incubating said mixture to form a substantially homogeneous population of a NABB associated with said recombinant membrane protein;

d) depleting said detergent(s) from said incubated mixture of step (c) to obtain a detergent depleted mixture comprising a substantially homogeneous population of NABB associated with at least one recombinant membrane protein, wherein the depletion step is completed within one hour of obtaining said incubated mixture of step (c); and;

e) purifying said substantially homogeneous population of NABB associated with at least one recombinant membrane protein from said detergent depleted mixture.

2. The method of claim 1, wherein said combining step of (b) comprises an exchange of any detergent and/or lipid and/or phospholipid present in said cell membrane protein fraction with another detergent and/or phospholipid.

3. The method of claim 1, wherein said purifying step comprises an immunopurification or affinity-based purification step.

4. The method of claim 1, wherein said Zebrafish apolipoprotein A-I comprises SEQ ID NO: 1, 3, 6-8, or 9.

5. An immunogenic composition comprising a nanoscale apolipoprotein bound phospholipid bilayer (NABB) associated with at least one recombinant membrane protein obtained by the method of claim 1, wherein said recombinant membrane protein is a CCR5 receptor.

6. The method of claim 1, wherein said recombinant membrane protein is a seven transmembrane domain (7-TM) integral membrane protein.

7. The method of claim 1, wherein said recombinant membrane protein is a CCR5 receptor.

8. The method of claim 1, wherein detergent depletion from the incubated mixture in step (d) is completed within about 30 minutes of obtaining the incubated mixture.

9. The method of claim 1, wherein said recombinant membrane protein is an integral membrane protein.

10. The method of claim 9, wherein detergent depletion from the incubated mixture in step (d) is completed within about 30 minutes of obtaining the incubated mixture.

11. The method of claim 1, wherein the detergent has a Critical Micelle Concentration (CMC) value of about 50 mM or less at a temperature of about 20 to 25 degrees centigrade.

12. The method of claim 1, wherein the obtaining and/or the depleting step are performed at a temperature of about 2° C. to about 30° C.

13. The method of claim 1, wherein the obtaining, combining, incubating, and depleting steps are performed at a temperature of about 4° C.

14. The method of claim 1, wherein the mixture of step (b) comprises a molar ratio of about 25:1 phospholipid(s):apolipoprotein A-I to about 200:1 phospholipid(s):apolipoprotein A-I.

* * * * *

SEQUENCE LISTING

```
<160> NUMBER OF SEQ ID NOS: 27

<210> SEQ ID NO 1
<211> LENGTH: 241
<212> TYPE: PRT
<213> ORGANISM: Danio rerio

<400> SEQUENCE: 1

Gln Ala Asp Ala Pro Thr Gln Leu Glu His Tyr Lys Ala Ala Ala Leu
1               5                   10                  15

Val Tyr Leu Asn Gln Val Lys Asp Gln Ala Glu Lys Ala Leu Asp Asn
            20                  25                  30

Leu Asp Gly Thr Asp Tyr Glu Gln Tyr Lys Leu Gln Leu Ser Glu Ser
```

```
            35                  40                  45
Leu Thr Lys Leu Gln Glu Tyr Ala Gln Thr Thr Ser Gln Ala Leu Thr
 50                  55                  60

Pro Tyr Ala Glu Thr Ile Ser Thr Gln Leu Met Glu Asn Thr Lys Gln
 65                  70                  75                  80

Leu Arg Glu Arg Val Met Thr Asp Val Glu Asp Leu Arg Ser Lys Leu
                 85                  90                  95

Glu Pro His Arg Ala Glu Leu Tyr Thr Ala Leu Gln Lys His Ile Asp
            100                 105                 110

Glu Tyr Arg Glu Lys Leu Glu Pro Val Phe Gln Glu Tyr Ser Ala Leu
        115                 120                 125

Asn Arg Gln Asn Ala Glu Gln Leu Arg Ala Lys Leu Glu Pro Leu Met
130                 135                 140

Asp Asp Ile Arg Lys Ala Phe Glu Ser Asn Ile Glu Glu Thr Lys Ser
145                 150                 155                 160

Lys Val Val Pro Met Val Glu Ala Val Arg Thr Lys Leu Thr Glu Arg
                165                 170                 175

Leu Glu Asp Leu Arg Thr Met Ala Ala Pro Tyr Ala Glu Glu Tyr Lys
            180                 185                 190

Glu Gln Leu Val Lys Ala Val Glu Ala Arg Glu Lys Ile Ala Pro
        195                 200                 205

His Thr Gln Asp Leu Gln Thr Arg Met Glu Pro Tyr Met Glu Asn Val
210                 215                 220

Arg Thr Thr Phe Ala Gln Met Tyr Glu Thr Ile Ala Lys Ala Ile Gln
225                 230                 235                 240

Ala

<210> SEQ ID NO 2
<211> LENGTH: 243
<212> TYPE: PRT
<213> ORGANISM: Homo sapiens

<400> SEQUENCE: 2

Asp Glu Pro Pro Gln Ser Pro Trp Asp Arg Val Lys Asp Leu Ala Thr
 1               5                  10                  15

Val Tyr Val Asp Val Leu Lys Asp Ser Gly Arg Asp Tyr Val Ser Gln
             20                  25                  30

Phe Glu Gly Ser Ala Leu Gly Lys Gln Leu Asn Leu Lys Leu Leu Asp
         35                  40                  45

Asn Trp Asp Ser Val Thr Ser Thr Phe Ser Lys Leu Arg Glu Gln Leu
 50                  55                  60

Gly Pro Val Thr Gln Glu Phe Trp Asp Asn Leu Glu Lys Glu Thr Glu
 65                  70                  75                  80

Gly Leu Arg Gln Glu Met Ser Lys Asp Leu Glu Glu Val Lys Ala Lys
                 85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
```

```
            165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln

<210> SEQ ID NO 3
<211> LENGTH: 241
<212> TYPE: PRT
<213> ORGANISM: Artificial Sequence
<220> FEATURE:
<223> OTHER INFORMATION: synthetic

<400> SEQUENCE: 3

Gln Ala Asp Ala Pro Thr Gln Leu Glu His Tyr Lys Ala Ala Ala Leu
1               5                   10                  15

Val Tyr Leu Asn Gln Val Lys Asp Cys Ala Glu Lys Ala Leu Asp Asn
            20                  25                  30

Leu Asp Gly Thr Asp Tyr Glu Gln Tyr Lys Leu Gln Leu Ser Glu Ser
        35                  40                  45

Leu Thr Lys Leu Gln Glu Tyr Ala Gln Thr Thr Ser Gln Ala Leu Thr
    50                  55                  60

Pro Tyr Ala Glu Thr Ile Ser Thr Gln Leu Met Glu Asn Thr Lys Gln
65                  70                  75                  80

Leu Arg Glu Arg Val Met Thr Asp Val Glu Asp Leu Arg Ser Lys Leu
                85                  90                  95

Glu Pro His Arg Ala Glu Leu Tyr Thr Ala Leu Gln Lys His Ile Asp
            100                 105                 110

Glu Tyr Arg Glu Lys Leu Glu Pro Val Phe Gln Glu Tyr Ser Ala Leu
        115                 120                 125

Asn Arg Gln Asn Ala Glu Gln Leu Arg Ala Lys Leu Glu Pro Leu Met
    130                 135                 140

Asp Asp Ile Arg Lys Ala Phe Glu Ser Asn Ile Glu Glu Thr Lys Ser
145                 150                 155                 160

Lys Val Val Pro Met Val Glu Ala Val Arg Thr Lys Leu Thr Glu Arg
                165                 170                 175

Leu Glu Asp Leu Arg Thr Met Ala Ala Pro Tyr Ala Glu Glu Tyr Lys
            180                 185                 190

Glu Gln Leu Val Lys Ala Val Glu Ala Arg Glu Lys Ile Ala Pro
        195                 200                 205

His Thr Gln Asp Leu Gln Thr Arg Met Glu Pro Tyr Met Glu Asn Val
    210                 215                 220

Arg Thr Thr Phe Ala Gln Met Tyr Glu Thr Ile Ala Lys Ala Ile Gln
225                 230                 235                 240

Ala

<210> SEQ ID NO 4
<211> LENGTH: 17
<212> TYPE: DNA
<213> ORGANISM: Artificial Sequence
<220> FEATURE:
```

-continued

```
<223> OTHER INFORMATION: synthetic

<400> SEQUENCE: 4
caggctgatg ccccgac                                                     17

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
ttatgcctgg atggccttgg                                                  20

<210> SEQ ID NO 6
<211> LENGTH: 241
<212> TYPE: PRT
<213> ORGANISM: Danio rerio

<400> SEQUENCE: 6
```

Gln Ala Asp Ala Pro Thr Gln Leu Glu His Tyr Lys Ala Ala Ala Leu
1               5                   10                  15

Val Tyr Leu Asn Gln Val Lys Asp Gln Ala Glu Lys Ala Leu Asp Asn
            20                  25                  30

Leu Asp Gly Thr Asp Tyr Glu Gln Tyr Lys Leu Gln Leu Ser Glu Ser
        35                  40                  45

Leu Thr Lys Leu Gln Glu Tyr Ala Gln Thr Thr Ser Gln Ala Leu Thr
    50                  55                  60

Pro Tyr Ala Glu Thr Ile Ser Thr Gln Leu Met Glu Asn Thr Lys Gln
65                  70                  75                  80

Leu Arg Glu Arg Val Met Thr Asp Val Glu Asp Leu Arg Ser Lys Leu
                85                  90                  95

Glu Pro His Arg Ala Glu Leu Tyr Thr Ala Leu Gln Lys His Ile Asp
            100                 105                 110

Glu Tyr Arg Glu Lys Leu Glu Pro Val Phe Gln Glu Tyr Ser Ala Leu
        115                 120                 125

Asn Arg Gln Asn Ala Glu Gln Leu Arg Ala Lys Leu Glu Pro Leu Met
    130                 135                 140

Asp Asp Ile Arg Lys Ala Phe Glu Ser Asn Ile Glu Glu Thr Lys Ser
145                 150                 155                 160

Lys Val Val Pro Met Val Glu Ala Val Arg Thr Lys Leu Thr Glu Arg
                165                 170                 175

Leu Glu Asp Leu Arg Thr Met Ala Ala Pro Tyr Ala Glu Glu Tyr Lys
            180                 185                 190

Glu Gln Leu Val Lys Ala Val Glu Ala Arg Glu Lys Ile Ala Pro
        195                 200                 205

His Thr Gln Asp Leu Gln Thr Arg Met Glu Pro Tyr Met Glu Asn Val
    210                 215                 220

Arg Thr Thr Phe Ala Gln Met Tyr Glu Thr Ile Ala Lys Ala Ile Gln
225                 230                 235                 240

Ala

```
<210> SEQ ID NO 7
<211> LENGTH: 241
<212> TYPE: PRT
<213> ORGANISM: Danio rerio
```

```
<400> SEQUENCE: 7

Gln Ala Asp Ala Pro Thr Gln Leu Glu His Tyr Lys Ala Ala Leu
1               5                   10                  15

Val Tyr Leu Asn Gln Val Lys Asp Gln Ala Glu Lys Ala Leu Asp Asn
                20                  25                  30

Leu Asp Gly Thr Asp Tyr Glu Gln Tyr Lys Leu Gln Leu Ser Glu Ser
            35                  40                  45

Leu Thr Lys Leu Gln Glu Tyr Ala Gln Thr Thr Ser Gln Ala Leu Thr
    50                  55                  60

Pro Tyr Ala Glu Thr Ile Ser Thr Gln Leu Met Glu Asn Thr Lys Gln
65                  70                  75                  80

Leu Arg Glu Arg Val Met Thr Asp Val Glu Asp Leu Arg Ser Lys Leu
                85                  90                  95

Glu Pro His Arg Ala Glu Leu Tyr Thr Ala Leu Gln Lys His Ile Asp
            100                 105                 110

Glu Tyr Arg Glu Lys Leu Glu Pro Val Phe Gln Glu Tyr Ser Ala Leu
        115                 120                 125

Asn Arg Gln Asn Ala Glu Gln Leu Arg Ala Lys Leu Glu Pro Leu Met
130                 135                 140

Asp Asp Ile Arg Lys Ala Phe Glu Ser Asn Ile Glu Glu Thr Lys Ser
145                 150                 155                 160

Lys Val Val Pro Met Val Glu Ala Val Arg Thr Lys Leu Thr Glu Arg
                165                 170                 175

Leu Glu Asp Leu Arg Thr Met Ala Ala Pro Tyr Ala Glu Glu Tyr Lys
            180                 185                 190

Glu Gln Leu Val Lys Ala Val Glu Glu Ala Arg Glu Lys Ile Ala Pro
        195                 200                 205

His Thr Gln Asp Leu Gln Thr Arg Met Glu Pro Tyr Met Glu Asn Val
    210                 215                 220

Arg Thr Thr Phe Ala Gln Met Tyr Glu Thr Ile Ala Lys Ala Ile Gln
225                 230                 235                 240

Ala

<210> SEQ ID NO 8
<211> LENGTH: 241
<212> TYPE: PRT
<213> ORGANISM: Danio rerio

<400> SEQUENCE: 8

Gln Ala Asp Ala Pro Thr Gln Leu Glu His Tyr Lys Ala Ala Leu
1               5                   10                  15

Val Tyr Leu Asn Gln Val Lys Asp Gln Ala Glu Lys Ala Leu Asp Asn
                20                  25                  30

Leu Asp Gly Thr Asp Tyr Glu Gln Tyr Lys Leu Gln Leu Ser Glu Ser
            35                  40                  45

Leu Thr Lys Leu Gln Glu Tyr Ala Gln Thr Thr Ser Gln Ala Leu Thr
    50                  55                  60

Pro Tyr Ala Glu Thr Ile Ser Thr Gln Leu Met Glu Asn Thr Lys Gln
65                  70                  75                  80

Leu Arg Glu Arg Val Met Thr Asp Val Glu Asp Leu Arg Ser Lys Leu
                85                  90                  95

Glu Pro His Arg Ala Glu Leu Tyr Thr Ala Leu Gln Lys His Ile Asp
            100                 105                 110

Glu Tyr Arg Glu Lys Leu Glu Pro Val Phe Gln Glu Tyr Ser Ala Leu
```

```
                115                 120                 125
Asn Arg Gln Asn Ala Glu Gln Leu Arg Ala Lys Leu Glu Pro Leu Met
    130                 135                 140

Asp Asp Ile Arg Lys Ala Phe Glu Ser Asn Ile Glu Glu Thr Lys Ser
145                 150                 155                 160

Lys Val Val Pro Met Val Glu Ala Val Arg Thr Lys Leu Thr Glu Arg
                165                 170                 175

Leu Glu Asp Leu Arg Thr Met Ala Ala Pro Tyr Ala Glu Glu Tyr Lys
                180                 185                 190

Glu Gln Leu Val Lys Ala Val Glu Glu Ala Arg Glu Lys Ile Ala Pro
                195                 200                 205

His Thr Gln Asp Leu Gln Thr Arg Met Glu Pro Tyr Met Glu Asn Val
                210                 215                 220

Arg Thr Thr Phe Ala Gln Met Tyr Glu Thr Ile Ala Lys Ala Ile Gln
225                 230                 235                 240

Ala

<210> SEQ ID NO 9
<211> LENGTH: 241
<212> TYPE: PRT
<213> ORGANISM: Danio rerio

<400> SEQUENCE: 9

Gln Ala Asp Ala Pro Thr Gln Leu Glu His Tyr Lys Ala Ala Ala Leu
1               5                   10                  15

Val Tyr Leu Asn Gln Val Lys Asp Gln Ala Glu Lys Ala Leu Asp Asn
                20                  25                  30

Leu Asp Gly Thr Asp Tyr Glu Gln Tyr Lys Leu Gln Leu Ser Glu Ser
            35                  40                  45

Leu Thr Lys Leu Gln Glu Tyr Ala Gln Thr Thr Ser Gln Ala Leu Thr
        50                  55                  60

Pro Tyr Ala Glu Thr Ile Ser Thr Gln Leu Met Glu Asn Thr Lys Gln
65                  70                  75                  80

Leu Arg Glu Arg Val Met Thr Asp Val Glu Asp Leu Arg Ser Lys Leu
                85                  90                  95

Glu Pro His Arg Ala Glu Leu Tyr Thr Ala Leu Gln Lys His Ile Asp
            100                 105                 110

Glu Tyr Arg Glu Lys Leu Glu Pro Val Phe Gln Glu Tyr Ser Ala Leu
        115                 120                 125

Asn Arg Gln Asn Ala Glu Gln Leu Arg Ala Lys Leu Glu Pro Leu Met
    130                 135                 140

Asp Asp Ile Arg Lys Ala Phe Glu Ser Asn Ile Glu Glu Thr Lys Ser
145                 150                 155                 160

Lys Val Val Pro Met Val Glu Ala Val Arg Thr Lys Leu Thr Glu Arg
                165                 170                 175

Leu Glu Asp Leu Arg Thr Met Ala Ala Pro Tyr Ala Glu Glu Tyr Lys
                180                 185                 190

Glu Gln Leu Val Lys Ala Val Glu Glu Ala Arg Glu Lys Ile Ala Pro
                195                 200                 205

His Thr Gln Asp Leu Gln Thr Arg Met Glu Pro Tyr Met Glu Asn Val
                210                 215                 220

Arg Thr Thr Phe Ala Gln Met Tyr Glu Thr Ile Ala Lys Ala Ile Gln
225                 230                 235                 240

Ala
```

<210> SEQ ID NO 10
<211> LENGTH: 242
<212> TYPE: PRT
<213> ORGANISM: Anguilla japonica

<400> SEQUENCE: 10

Gln Ala Asp Ala Pro Ala Pro Pro Ser Gln Leu Glu His Val Arg Ala
1               5                   10                  15
Ala Val Gly Met Tyr Leu Gln Gln Val Lys Glu Thr Ala Gln Lys Ala
            20                  25                  30
Leu Glu His Leu Asp Asp Thr Glu Tyr Lys Asp Tyr Lys Leu Arg Leu
        35                  40                  45
Ser Gln Ser Leu Asp Asn Ile Gln Gly Tyr Ile Gln Ser Ala Ser Ala
    50                  55                  60
Ala Leu Ser Pro Tyr Thr Asp Ala Val Ser Ser Gln Phe Met Glu Leu
65                  70                  75                  80
Thr Lys Asp Met Arg Asp Lys Ile Gln Ala Asp Val Asp Gln Leu Lys
                85                  90                  95
Lys Asp Leu Gln Pro Lys Arg Asp Glu Leu Lys Glu Val Val Gln Lys
            100                 105                 110
His Leu Asp Glu Tyr Arg Ala Lys Leu Glu Pro Leu Val Lys Glu Tyr
        115                 120                 125
Thr Glu Lys His Lys Gln Glu Met Glu Glu Leu Lys Thr Lys Leu Gln
    130                 135                 140
Pro Val Val Glu Asp Leu Arg Ala Arg Ile Gln Val Asn Val Glu Glu
145                 150                 155                 160
Thr Lys Ser Lys Leu Val Pro Ile Val Glu Ala Ile Arg Ala Lys Leu
                165                 170                 175
Thr Glu Arg Leu Glu Glu Leu Arg Thr Leu Ala Glu Pro Tyr Val Gln
            180                 185                 190
Glu Tyr Lys Asp His Leu Ser Glu Ala Leu Thr Asp Val Lys Asp Lys
        195                 200                 205
Val Gln Gly Glu Asp Leu Gln Ser Lys Leu Lys Pro Tyr Ala Glu Glu
    210                 215                 220
Leu Lys Thr Lys Leu Val Ala Leu Trp Glu Ser Leu Ser Gln Pro Lys
225                 230                 235                 240
Ala Ser

<210> SEQ ID NO 11
<211> LENGTH: 242
<212> TYPE: PRT
<213> ORGANISM: Anguilla japonica

<400> SEQUENCE: 11

Gln Ala Asp Ala Pro Ala Pro Pro Ser Gln Leu Glu His Val Arg Ala
1               5                   10                  15
Ala Val Gly Met Tyr Leu Gln Gln Val Lys Glu Thr Ala Gln Lys Ala
            20                  25                  30
Leu Glu His Leu Asp Asp Thr Glu Tyr Lys Asp Tyr Lys Leu Arg Leu
        35                  40                  45
Ser Gln Ser Leu Asp Asn Ile Gln Gly Tyr Ile Gln Ser Ala Ser Ala
    50                  55                  60
Ala Leu Ser Pro Tyr Thr Asp Ala Val Ser Ser Gln Phe Met Glu Leu
65                  70                  75                  80

Thr Lys Asp Met Arg Asp Lys Ile Gln Ala Asp Val Asp Gln Leu Lys
                85                  90                  95

Lys Asp Leu Gln Pro Lys Arg Asp Glu Leu Lys Glu Val Val Gln Lys
            100                 105                 110

His Leu Asp Glu Tyr Arg Ala Lys Leu Glu Pro Leu Val Lys Glu Tyr
        115                 120                 125

Thr Glu Lys His Lys Gln Glu Met Glu Glu Leu Lys Thr Lys Leu Gln
    130                 135                 140

Pro Val Val Glu Asp Leu Arg Ala Arg Ile Gln Val Asn Val Glu Glu
145                 150                 155                 160

Thr Lys Ser Lys Leu Val Pro Ile Val Glu Ala Ile Arg Ala Lys Leu
                165                 170                 175

Thr Glu Arg Leu Glu Glu Leu Arg Thr Leu Ala Glu Pro Tyr Val Gln
            180                 185                 190

Glu Tyr Lys Asp His Leu Ser Glu Ala Leu Thr Asp Val Lys Asp Lys
        195                 200                 205

Val Gln Gly Glu Asp Leu Gln Ser Lys Leu Lys Pro Tyr Ala Glu Glu
    210                 215                 220

Leu Lys Thr Lys Leu Val Ala Leu Trp Glu Ser Leu Ser Gln Pro Lys
225                 230                 235                 240

Ala Ser

<210> SEQ ID NO 12
<211> LENGTH: 174
<212> TYPE: PRT
<213> ORGANISM: Cyprinus carpio

<400> SEQUENCE: 12

Leu Gly Gln Ser Val Asp Asn Leu His Gly Tyr Phe Gln Asn Gly Phe
1               5                   10                  15

Gln Ala Ile Thr Pro Ile Gly Asp Gln Val Leu Glu Ala Thr Lys Asp
            20                  25                  30

Thr Arg Glu Lys Leu Val Lys Asp Val Glu Glu Leu Arg Lys Lys Ile
        35                  40                  45

Glu Pro Met Arg Ala Glu Leu Arg Gln Val Leu Glu Lys His Leu Gln
    50                  55                  60

Glu Tyr Arg Asp Glu Leu Lys Pro Phe Val Glu Glu Tyr Leu Thr Lys
65                  70                  75                  80

His Gln Lys Phe Leu Glu Glu Met Arg Ile Lys Leu Glu Pro Val Val
                85                  90                  95

Lys Ser Leu Arg Glu Lys Phe Gly Pro Asn Trp Glu Glu Thr Lys Ser
            100                 105                 110

Lys Leu Met Pro Ile Leu Glu Ala Val Arg Glu Lys Val Ala Glu His
        115                 120                 125

Leu Gln Asp Leu Lys Lys Leu Leu Glu Pro Tyr Met Gln Asp Tyr Arg
    130                 135                 140

Glu Gln Met Glu Lys Gly Ala Gln Glu Phe Arg Gln Ser Val Lys Ser
145                 150                 155                 160

Gly Glu Leu Arg Lys Lys Met Asn Glu Leu Gly Arg Arg Arg
                165                 170

<210> SEQ ID NO 13
<211> LENGTH: 241
<212> TYPE: PRT
<213> ORGANISM: Oncorhynchus mykiss

<400> SEQUENCE: 13

```
Gln Ala Asp Ala Pro Ser Gln Leu Glu His Val Lys Ala Ala Leu Ser
1               5                   10                  15

Met Tyr Ile Ala Gln Val Lys Leu Thr Ala Gln Arg Ser Ile Asp Leu
            20                  25                  30

Leu Asp Asp Thr Glu Tyr Lys Glu Tyr Lys Met Gln Leu Thr Gln Ser
        35                  40                  45

Leu Asp Asn Leu Gln Gln Tyr Ala Asp Ala Thr Ser Gln Ser Leu Ala
    50                  55                  60

Pro Tyr Ser Glu Ala Phe Gly Thr Gln Leu Thr Asp Ala Thr Ala Ala
65                  70                  75                  80

Val Arg Ala Glu Val Met Lys Asp Val Glu Glu Leu Arg Ser Gln Leu
                85                  90                  95

Glu Pro Lys Arg Ala Glu Leu Lys Glu Val Leu Asp Lys His Ile Asp
            100                 105                 110

Glu Tyr Arg Lys Lys Leu Glu Pro Leu Ile Lys Glu His Ile Glu Leu
        115                 120                 125

Arg Arg Thr Glu Met Glu Ala Phe Arg Ala Lys Met Glu Pro Ile Val
130                 135                 140

Glu Glu Leu Arg Ala Lys Val Ala Ile Asn Val Glu Glu Thr Lys Thr
145                 150                 155                 160

Lys Leu Met Pro Ile Val Glu Ile Val Arg Ala Lys Leu Thr Glu Arg
                165                 170                 175

Leu Glu Glu Leu Arg Thr Leu Ala Ala Pro Tyr Ala Glu Glu Tyr Lys
            180                 185                 190

Glu Gln Met Ile Lys Ala Val Gly Glu Val Arg Glu Lys Val Ser Pro
        195                 200                 205

Leu Ser Glu Asp Phe Lys Gly Gln Val Gly Pro Ala Ala Glu Gln Ala
    210                 215                 220

Lys Gln Lys Leu Leu Ala Phe Tyr Glu Thr Ile Ser Gln Ala Met Lys
225                 230                 235                 240

Ala
```

<210> SEQ ID NO 14
<211> LENGTH: 241
<212> TYPE: PRT
<213> ORGANISM: Oncorhynchus mykiss

<400> SEQUENCE: 14

```
Gln Ala Asp Ala Pro Ser Gln Leu Glu His Val Lys Ala Ala Leu Ser
1               5                   10                  15

Met Tyr Ile Ala Gln Val Lys Leu Thr Ala Gln Arg Ser Ile Asp Leu
            20                  25                  30

Leu Asp Asp Thr Glu Tyr Lys Glu Tyr Lys Met Gln Leu Thr Gln Ser
        35                  40                  45

Leu Asp Asn Leu Gln Gln Tyr Ala Asp Ala Thr Ser Gln Ser Leu Ala
    50                  55                  60

Pro Tyr Ser Glu Ala Phe Gly Thr Gln Leu Thr Asp Ala Thr Ala Ala
65                  70                  75                  80

Val Arg Ala Glu Val Met Lys Asp Val Glu Glu Leu Arg Ser Gln Leu
                85                  90                  95

Glu Pro Lys Arg Ala Glu Leu Lys Glu Val Leu Asp Lys His Ile Asp
            100                 105                 110

Glu Tyr Arg Lys Lys Leu Glu Pro Leu Ile Lys Glu His Ile Glu Leu
```

```
            115                 120                 125
Arg Arg Thr Glu Met Glu Ala Phe Arg Ala Lys Met Glu Pro Ile Val
    130                 135                 140

Glu Glu Leu Arg Ala Lys Val Ala Ile Asn Val Glu Thr Lys Thr
145                 150                 155                 160

Lys Leu Met Pro Ile Val Glu Ile Val Arg Ala Lys Leu Thr Glu Arg
                165                 170                 175

Leu Glu Glu Leu Arg Thr Leu Ala Ala Pro Tyr Ala Glu Glu Tyr Lys
            180                 185                 190

Glu Gln Met Ile Lys Ala Val Gly Glu Val Arg Glu Lys Val Ser Pro
        195                 200                 205

Leu Ser Glu Asp Phe Lys Gly Gln Val Gly Pro Ala Ala Glu Gln Ala
    210                 215                 220

Lys Gln Lys Leu Leu Ala Phe Tyr Glu Thr Ile Ser Gln Ala Met Lys
225                 230                 235                 240

Ala

<210> SEQ ID NO 15
<211> LENGTH: 241
<212> TYPE: PRT
<213> ORGANISM: Oncorhynchus mykiss

<400> SEQUENCE: 15

Gln Ala Asp Ala Pro Ser Gln Leu Glu His Val Lys Val Ala Met Met
1               5                   10                  15

Glu Tyr Met Ala Gln Val Lys Glu Thr Ala Gln Arg Ser Ile Asp His
            20                  25                  30

Leu Asp Asp Thr Glu Tyr Lys Glu Tyr Lys Val Gln Leu Ser Gln Ser
        35                  40                  45

Leu Asp Asn Leu Gln Gln Tyr Ala Gln Thr Ala Ser Glu Ser Leu Ala
    50                  55                  60

Pro Tyr Ser Glu Ala Ile Gly Val Gln Leu Thr Glu Ala Thr Ala Ala
65                  70                  75                  80

Val Arg Ala Glu Val Met Lys Asp Val Glu Glu Leu Arg Ser Gln Leu
                85                  90                  95

Glu Pro Lys Arg Ala Glu Leu Lys Glu Val Leu Asp Lys His Ile Asp
            100                 105                 110

Glu Tyr Arg Lys Arg Leu Glu Pro Leu Ile Lys Asp Ile Val Glu Gln
        115                 120                 125

Arg Arg Thr Glu Leu Glu Ala Phe Arg Val Lys Ile Glu Pro Val Val
    130                 135                 140

Glu Glu Met Arg Ala Lys Val Ser Ala Asn Val Glu Glu Thr Lys Ala
145                 150                 155                 160

Lys Leu Met Pro Ile Val Glu Thr Val Arg Ala Lys Leu Thr Glu Arg
                165                 170                 175

Leu Glu Glu Leu Arg Thr Leu Ala Ser Pro Tyr Ala Glu Glu Tyr Lys
            180                 185                 190

Glu Gln Met Val Lys Ala Val Gly Glu Val Arg Glu Lys Val Val Pro
        195                 200                 205

Leu Thr Thr Asp Phe Lys Gly Gln Leu Gly Pro Ala Ala Glu Gln Ala
    210                 215                 220

Lys Glu Lys Leu Met Ala Leu Tyr Glu Thr Ile Ser Gln Ala Met Lys
225                 230                 235                 240

Ala
```

<210> SEQ ID NO 16
<211> LENGTH: 140
<212> TYPE: PRT
<213> ORGANISM: Morone saxatilis

<400> SEQUENCE: 16

```
Leu Lys Glu Val Ile Asp Lys His Ile Ser Glu Tyr Arg Thr Leu Met
1               5                   10                  15

Asp Pro Ile Leu Thr Glu Tyr Tyr Ala Lys His Thr Ala Asp Met Glu
            20                  25                  30

Ala Leu Lys Leu Lys Met Glu Pro Ile Val Glu Glu Leu Arg Thr Lys
        35                  40                  45

Ile Ser Thr Asn Val Glu Glu Thr Lys Thr Ala Leu Met Pro Ile Val
    50                  55                  60

Glu Ser Val Arg Asp Lys Leu Gln Glu Arg Leu Glu Ser Leu Lys Ala
65                  70                  75                  80

Met Ala Ser Pro Tyr Val Glu Glu Tyr Lys Gln Leu Lys Gln Ala
                85                  90                  95

Tyr Asn Gln Ala Gln Asn Ile Asn Ala Asp Glu Ile Thr Thr Leu Lys
            100                 105                 110

Asp Lys Ile Thr Pro Leu Ala Glu Glu Val Lys Ala Lys Leu Gln Glu
        115                 120                 125

Ile Phe Glu Ala Ile Ala Ala Ser Ile Thr Lys Asn
    130                 135                 140
```

<210> SEQ ID NO 17
<211> LENGTH: 169
<212> TYPE: PRT
<213> ORGANISM: Morone saxatilis

<400> SEQUENCE: 17

```
Gln Ala Asp Ala Pro Ser Gln Leu Ala His Val Arg Ala Ala Met Asp
1               5                   10                  15

Val Tyr Leu Thr Gln Val Glu Asp Ser Ala Asn Lys Ala Leu Asp Gln
            20                  25                  30

Leu Asp Asp Thr Glu Tyr Lys Glu Leu Lys Ala Thr Leu Ser Gln Arg
        35                  40                  45

Leu Glu Asp Met Tyr Asn Gln Val Lys Thr Leu Gln Gly Ala Val Ser
    50                  55                  60

Pro Met Thr Asp Ser Val Val Ser Thr Ile Ser Asp Ala Thr Ala Glu
65                  70                  75                  80

Phe Arg Ala Ser Val Leu Ala Asp Ile Glu Ala Leu Lys Ala Asp Leu
                85                  90                  95

Ala Pro Lys Gln Val Gln Leu Lys Glu Val Ile Asp Lys His Ile Ser
            100                 105                 110

Glu Tyr Arg Thr Leu Met Asp Pro Ile Leu Thr Glu Tyr Tyr Ala Lys
        115                 120                 125

His Thr Ala Asp Met Glu Ala Leu Lys Leu Lys Met Glu Pro Ile Val
    130                 135                 140

Glu Glu Leu Arg Thr Lys Ile Ser Thr Asn Val Glu Glu Thr Lys Thr
145                 150                 155                 160

Ala Leu Met Pro Ile Val Glu Ser Val
                165
```

<210> SEQ ID NO 18

```
<211> LENGTH: 182
<212> TYPE: PRT
<213> ORGANISM: Morone saxatilis

<400> SEQUENCE: 18

Val Arg Ala Ala Met Asp Val Tyr Leu Thr Gln Val Glu Asp Ser Ala
1               5                   10                  15

Asn Lys Ala Leu Asp Gln Leu Asp Asp Thr Glu Tyr Lys Glu Leu Lys
            20                  25                  30

Ala Thr Leu Ser Gln Arg Leu Glu Asp Met Tyr Asn Gln Val Lys Thr
        35                  40                  45

Leu Gln Gly Ala Val Ser Pro Met Thr Asp Ser Val Val Ser Thr Ile
    50                  55                  60

Ser Asp Ala Thr Ala Glu Phe Arg Ala Ser Val Leu Ala Asp Ile Glu
65                  70                  75                  80

Ala Leu Lys Ala Asp Leu Ala Pro Lys Gln Val Gln Leu Lys Glu Val
                85                  90                  95

Ile Asp Lys His Ile Ser Glu Tyr Arg Thr Leu Met Asp Pro Ile Leu
            100                 105                 110

Thr Glu Tyr Tyr Ala Lys His Thr Ala Asp Met Glu Ala Leu Lys Leu
        115                 120                 125

Lys Met Glu Pro Ile Val Glu Glu Leu Arg Thr Lys Ile Ser Thr Asn
    130                 135                 140

Val Glu Glu Thr Lys Thr Ala Leu Met Pro Ile Val Glu Ser Val Arg
145                 150                 155                 160

Asp Lys Leu Gln Glu Arg Leu Glu Ser Leu Lys Ala Met Ala Ser Pro
                165                 170                 175

Tyr Pro Glu Glu Tyr Lys
            180

<210> SEQ ID NO 19
<211> LENGTH: 111
<212> TYPE: PRT
<213> ORGANISM: Gadus morhua

<400> SEQUENCE: 19

Gln Ser Asp Ala Pro Ser Gln Leu Ala His Ile Arg Ser Ala Val Gly
1               5                   10                  15

Met Tyr Leu Asp Gln Val Lys Asp Ser Ala Ala Arg Ser Leu Asp His
            20                  25                  30

Leu Asp Gly Thr Glu Tyr Glu Ser Tyr Lys Ala Gln Leu Ala Thr Ser
        35                  40                  45

Leu Asp Ser Leu Gln Ala Ser Ile Lys Thr Ala Gln Ala Gly Ala Glu
    50                  55                  60

Pro Tyr Thr Asp Ala Ala Val Ala Gln Val Met Glu Ala Thr Thr Glu
65                  70                  75                  80

Val Arg Ala Ser Ile Met Ala Asp Ile Glu Thr Leu Arg Thr Gly Pro
                85                  90                  95

Gly Pro Lys Arg Glu Ala Leu Lys Lys Val Val Asp Gly His Ile
            100                 105                 110

<210> SEQ ID NO 20
<211> LENGTH: 237
<212> TYPE: PRT
<213> ORGANISM: Salmo salar

<400> SEQUENCE: 20
```

Gln Ala Asp Ala Pro Ser Gln Leu Glu His Val Lys Ala Ala Leu Asn
1               5                   10                  15

Met Tyr Ile Ala Gln Val Lys Leu Thr Ala Gln Arg Ser Ile Asp Leu
            20                  25                  30

Leu Asp Asp Thr Glu Tyr Lys Glu Tyr Lys Met Gln Leu Ser Gln Ser
            35                  40                  45

Leu Asp Asn Leu Gln Gln Phe Ala Asp Ser Thr Ser Lys Ser Trp Pro
50                      55                  60

Pro Thr Pro Arg Ser Ser Ala Pro Ser Cys Asp Ala Thr Ala Thr Val
65                  70                  75                  80

Arg Ala Glu Val Met Lys Asp Val Glu Asp Val Arg Thr Gln Leu Glu
                85                  90                  95

Pro Lys Arg Ala Glu Leu Thr Glu Val Leu Asn Lys His Ile Asp Glu
            100                 105                 110

Tyr Arg Lys Lys Leu Glu Pro Leu Ile Lys Gln His Ile Glu Leu Arg
            115                 120                 125

Arg Thr Glu Met Asp Ala Phe Arg Ala Lys Ile Asp Pro Val Val Glu
            130                 135                 140

Glu Met Arg Ala Lys Val Ala Val Asn Val Glu Glu Thr Lys Thr Lys
145                 150                 155                 160

Leu Met Pro Ile Val Glu Ile Val Arg Ala Lys Leu Thr Glu Arg Leu
                165                 170                 175

Glu Glu Leu Arg Thr Leu Ala Ala Pro Tyr Ala Glu Glu Tyr Lys Glu
                180                 185                 190

Gln Met Phe Lys Ala Val Gly Glu Val Arg Lys Val Ala Pro Leu
            195                 200                 205

Ser Glu Asp Phe Lys Ala Arg Trp Ala Pro Pro Arg Arg Pro Ser
210                 215                 220

Lys Ser Ser Trp Leu Ser Thr Arg Pro Ser Ala Arg Pro
225                 230                 235

<210> SEQ ID NO 21
<211> LENGTH: 241
<212> TYPE: PRT
<213> ORGANISM: Salmo salar

<400> SEQUENCE: 21

Gln Ala Asp Ala Pro Ser Gln Leu Glu His Val Lys Val Ala Met Met
1               5                   10                  15

Glu Tyr Met Ala Gln Val Lys Glu Thr Ala Gln Arg Ser Ile Asp Leu
            20                  25                  30

Leu Asp Asp Thr Glu Phe Lys Glu Tyr Lys Val Gln Leu Ser Gln Ser
            35                  40                  45

Leu Asp Asn Leu Gln Gln Tyr Ala Gln Thr Thr Ser Gln Ser Leu Ala
50                      55                  60

Pro Tyr Ser Glu Ala Phe Gly Ala Gln Leu Thr Asp Ala Ala Ala Ala
65                  70                  75                  80

Val Arg Ala Glu Val Met Lys Asp Val Glu Glu Leu Arg Thr Gln Leu
                85                  90                  95

Glu Pro Lys Arg Ala Glu Leu Lys Glu Val Leu Asp Lys His Ile Asp
            100                 105                 110

Glu Tyr Arg Lys Lys Leu Glu Pro Leu Ile Lys Glu Ile Val Glu Gln
            115                 120                 125

Arg Arg Thr Glu Leu Glu Ala Phe Arg Val Lys Met Glu Pro Val Val
            130                 135                 140

```
Glu Glu Met Arg Ala Lys Val Ser Thr Asn Val Glu Thr Lys Ala
145                 150                 155                 160

Lys Leu Met Pro Ile Val Glu Thr Val Arg Ala Lys Leu Thr Glu Arg
                165                 170                 175

Leu Glu Glu Leu Arg Thr Leu Ala Ala Pro Tyr Ala Glu Tyr Lys
            180                 185                 190

Glu Gln Met Phe Lys Ala Val Gly Glu Val Arg Glu Lys Val Gly Pro
            195                 200                 205

Leu Thr Asn Asp Phe Lys Gly Gln Val Gly Pro Ala Ala Glu Gln Ala
            210                 215                 220

Lys Glu Lys Leu Met Ala Phe Tyr Glu Thr Ile Ser Gln Ala Ile Lys
225                 230                 235                 240

Ala
```

<210> SEQ ID NO 22
<211> LENGTH: 241
<212> TYPE: PRT
<213> ORGANISM: Salmo salar

<400> SEQUENCE: 22

```
Gln Ala Asp Ala Pro Ser Gln Leu Glu His Val Lys Val Ala Met Met
1               5                   10                  15

Glu Tyr Met Ala Gln Val Lys Glu Thr Ala Gln Arg Ser Ile Asp Leu
            20                  25                  30

Leu Asp Asp Thr Glu Phe Lys Glu Tyr Lys Val Gln Leu Ser Gln Ser
        35                  40                  45

Leu Asp Asn Leu Gln Gln Tyr Ala Gln Thr Thr Ser Gln Ser Leu Ala
    50                  55                  60

Pro Tyr Ser Glu Ala Phe Gly Ala Gln Leu Thr Asp Ala Ala Ala Ala
65                  70                  75                  80

Val Arg Ala Glu Val Met Lys Asp Val Glu Glu Leu Arg Thr Gln Leu
                85                  90                  95

Glu Pro Lys Arg Ala Glu Leu Lys Glu Val Leu Asp Lys His Ile Asp
            100                 105                 110

Glu Tyr Arg Lys Lys Leu Glu Pro Leu Ile Lys Glu Ile Val Glu Gln
        115                 120                 125

Arg Arg Thr Glu Leu Glu Ala Phe Arg Val Lys Met Glu Pro Val Val
    130                 135                 140

Glu Glu Met Arg Ala Lys Val Ser Thr Asn Val Glu Glu Thr Lys Ala
145                 150                 155                 160

Lys Leu Met Pro Ile Val Glu Thr Val Arg Ala Lys Leu Thr Glu Arg
                165                 170                 175

Leu Glu Glu Leu Arg Thr Leu Ala Ala Pro Tyr Ala Glu Tyr Lys
            180                 185                 190

Glu Gln Met Phe Lys Ala Val Gly Glu Val Arg Glu Lys Val Gly Pro
            195                 200                 205

Leu Thr Asn Asp Phe Lys Gly Gln Val Gly Pro Ala Ala Glu Gln Ala
            210                 215                 220

Lys Glu Lys Leu Met Ala Phe Tyr Glu Thr Ile Ser Gln Ala Ile Lys
225                 230                 235                 240

Ala
```

<210> SEQ ID NO 23
<211> LENGTH: 242

```
<212> TYPE: PRT
<213> ORGANISM: Takifugu rubripes

<400> SEQUENCE: 23

Met Ala Asp Pro Pro Ser Glu Leu Glu His Phe Arg Ser Ala Leu Ser
1               5                   10                  15

Met Tyr Leu Asp Arg Ala Lys Glu Arg Ala His Ser Ala Leu Ala Thr
            20                  25                  30

Leu Asp Asp Ala Glu Tyr Lys Glu Leu Lys Asp Arg Leu Ala Gln Arg
        35                  40                  45

Val Asp Asp Ile His Ser Gln Ile Lys Thr Leu Gln Gly Ser Val Ser
    50                  55                  60

Pro Ile Thr Asp Ser Val Val Ser Thr Ile Ser Asp Ala Thr Ser Glu
65                  70                  75                  80

Leu Arg Thr Ser Ile Gln Thr Asp Phe Lys Thr Leu Gln Asp Glu Thr
                85                  90                  95

Ala Ala Gln Arg Glu Lys Leu Arg Ala Val Val Glu Gln His Leu Ser
            100                 105                 110

Glu Tyr Arg Thr Leu Leu Gln Pro Ile Val Ser Glu Tyr Gln Ala Lys
        115                 120                 125

His Lys Glu Glu Met Asp Ala Leu Lys Leu Lys Leu Asp Pro Val Met
    130                 135                 140

Glu Glu Leu His Lys Lys Ile Ala Val Asn Val Glu Glu Thr Lys Gly
145                 150                 155                 160

Ala Leu Met Pro Ile Val Glu Lys Val His Thr Lys Leu Ala Glu Tyr
                165                 170                 175

Val Glu Gln Ile Lys Ala Val Val Thr Pro Tyr Val Asn Glu Tyr Lys
            180                 185                 190

Glu Glu Leu Arg Asp Thr Tyr Ile Arg Ala Met Ser Leu Ser Arg Asp
        195                 200                 205

Asp Leu Asp Ala Met Arg Ser Lys Ile Asp Pro Ile Val Glu Val Ile
    210                 215                 220

Lys Glu Lys Val Gly Glu Ile Gly Gln Ile Val Ser Ser Thr Phe Ser
225                 230                 235                 240

Lys Ser

<210> SEQ ID NO 24
<211> LENGTH: 242
<212> TYPE: PRT
<213> ORGANISM: Takifugu rubripes

<400> SEQUENCE: 24

Met Ala Asp Pro Pro Ser Glu Leu Glu His Phe Arg Ser Ala Leu Ser
1               5                   10                  15

Met Tyr Leu Asp Arg Ala Lys Glu Arg Ala His Ser Ala Leu Ala Thr
            20                  25                  30

Leu Asp Asp Ala Glu Tyr Lys Glu Leu Lys Asp Arg Leu Ala Gln Arg
        35                  40                  45

Val Asp Asp Ile His Ser Gln Ile Lys Thr Leu Gln Gly Ser Val Ser
    50                  55                  60

Pro Ile Thr Asp Ser Val Val Ser Thr Ile Ser Asp Ala Thr Ser Glu
65                  70                  75                  80

Leu Arg Thr Ser Ile Gln Thr Asp Phe Lys Thr Leu Gln Asp Glu Thr
                85                  90                  95

Ala Ala Gln Arg Glu Lys Leu Arg Ala Val Val Glu Gln His Leu Ser
```

```
                100                 105                 110
Glu Tyr Arg Thr Leu Leu Gln Pro Ile Val Ser Glu Tyr Gln Ala Lys
            115                 120                 125

His Lys Glu Glu Met Asp Ala Leu Lys Leu Lys Leu Asp Pro Val Met
130                 135                 140

Glu Glu Leu His Lys Lys Ile Ala Val Asn Val Glu Glu Thr Lys Gly
145                 150                 155                 160

Ala Leu Met Pro Ile Val Glu Lys Val His Thr Lys Leu Ala Glu Tyr
                165                 170                 175

Val Glu Gln Ile Lys Ala Val Val Thr Pro Tyr Val Asn Glu Tyr Lys
            180                 185                 190

Glu Glu Leu Arg Asp Thr Tyr Ile Arg Ala Met Ser Leu Ser Arg Asp
            195                 200                 205

Asp Leu Asp Ala Met Arg Ser Lys Ile Asp Pro Ile Val Glu Val Ile
            210                 215                 220

Lys Glu Lys Val Gly Glu Ile Gly Gln Ile Val Ser Ser Thr Phe Ser
225                 230                 235                 240

Lys Ser

<210> SEQ ID NO 25
<211> LENGTH: 8
<212> TYPE: PRT
<213> ORGANISM: Artificial sequence
<220> FEATURE:
<223> OTHER INFORMATION: synthetic

<400> SEQUENCE: 25

Met Met His His His His His His
1               5

<210> SEQ ID NO 26
<211> LENGTH: 8
<212> TYPE: PRT
<213> ORGANISM: Artificial sequence
<220> FEATURE:
<223> OTHER INFORMATION: synthetic

<400> SEQUENCE: 26

Leu Glu Val Leu Phe Gln Gly Pro
1               5

<210> SEQ ID NO 27
<211> LENGTH: 4
<212> TYPE: PRT
<213> ORGANISM: Artificial sequence
<220> FEATURE:
<223> OTHER INFORMATION: synthetic

<400> SEQUENCE: 27

Ile Glu Gly Arg
1
```